US012426907B2

(12) United States Patent
Strauss et al.

(10) Patent No.: US 12,426,907 B2
(45) Date of Patent: Sep. 30, 2025

(54) SYSTEMS AND METHODS FOR CONTROLLABLE ACCESS OF TOOLS TO ELEVATED TISSUES

(71) Applicant: MICROSTEER LTD, Nazareth (IL)

(72) Inventors: Adi Strauss, Alonei Abba Village (IL); Ofer Pillar, Kiryat Haim-Haifa (IL); Victor Levin, Haifa (IL); Gonen Yuval, Kiryat Tiv'on (IL); Gil Katz, Avtalion (IL)

(73) Assignee: Microsteer LTD., Nazareth (IL)

( * ) Notice: Subject to any disclaimer, the term of this patent is extended or adjusted under 35 U.S.C. 154(b) by 573 days.

(21) Appl. No.: 17/778,267

(22) PCT Filed: Nov. 22, 2020

(86) PCT No.: PCT/IL2020/051204
§ 371 (c)(1),
(2) Date: May 19, 2022

(87) PCT Pub. No.: WO2021/100049
PCT Pub. Date: May 27, 2021

(65) Prior Publication Data
US 2022/0387061 A1 Dec. 8, 2022

Related U.S. Application Data

(60) Provisional application No. 62/939,595, filed on Nov. 23, 2019, provisional application No. 62/939,312, filed on Nov. 22, 2019.

(51) Int. Cl.
*A61B 17/32* (2006.01)
*A61B 1/00* (2006.01)
(Continued)

(52) U.S. Cl.
CPC .... *A61B 17/320016* (2013.01); *A61B 1/0004* (2022.02); *A61B 1/018* (2013.01);
(Continued)

(58) Field of Classification Search
CPC ......... A61B 1/0004; A61B 1/018; A61B 1/05; A61B 1/0676; A61B 17/320016; A61B 1/00087; A61B 1/041
See application file for complete search history.

(56) References Cited

U.S. PATENT DOCUMENTS 5,443,474 A * 8/1995 Sfakianos ...... A61B 17/320016
30/294
5,984,860 A * 11/1999 Shan ...................... A61B 1/041
600/116
(Continued)

FOREIGN PATENT DOCUMENTS

JP          2007517590 A     7/2007

*Primary Examiner* — Aaron B Fairchild
(74) *Attorney, Agent, or Firm* — William H. Dippert; Laurence A. Greenberg; Werner H. Stemer

(57) ABSTRACT

The present subject matter provides a system for allowing controlled access of a tool to all sides of an elevated tissue in a body of a patient, the system including: a rail configured to surround the elevated tissue; and at least one vehicle configured to move along the rail and carry at least one tool configured to manipulate the elevated tissue. Also provided is a method for cutting an elevated tissue in a body of a patient, the method including: inserting a rail to a vicinity of the elevated tissue; surrounding the elevated tissue with the rail; placing a vehicle on the rail; connecting a cutting device to the vehicle; and moving the vehicle along the rail while cutting the elevated tissue with the cutting device. Additional embodiments of the system and method are disclosed herein.

25 Claims, 26 Drawing Sheets

(51) Int. Cl.
*A61B 1/018* (2006.01)
*A61B 1/05* (2006.01)
*A61B 1/06* (2006.01)
*A61B 17/00* (2006.01)

(52) U.S. Cl.
CPC .............. *A61B 1/05* (2013.01); *A61B 1/0676* (2013.01); *A61B 2017/00398* (2013.01); *A61B 2017/320052* (2013.01); *A61B 2017/32006* (2013.01)

(56) References Cited

U.S. PATENT DOCUMENTS

| | | |
|---|---|---|
| 8,128,592 B2 | 3/2012 | Mitelberg et al. |
| 9,955,854 B2 | 5/2018 | Trabada et al. |
| 2004/0133089 A1* | 7/2004 | Kilcoyne ........... A61B 5/14546 600/350 |
| 2006/0253128 A1* | 11/2006 | Sekine ............. A61B 17/32056 606/139 |
| 2013/0172828 A1 | 7/2013 | Kappel et al. |
| 2015/0157352 A1* | 6/2015 | Thistle ............. A61B 17/32002 606/170 |
| 2016/0228113 A1 | 8/2016 | Weitzner et al. |
| 2019/0046021 A1 | 2/2019 | Charles et al. |

* cited by examiner

SYSTEMS AND METHODS FOR CONTROLLABLE ACCESS OF TOOLS TO ELEVATED TISSUES

CROSS-REFERENCE TO RELATED PATENT APPLICATIONS

This patent application is a U.S. National Phase filing under 35 U.S.C. § 371 of PCT Patent Application No. PCT/IL2020/051204, filed Nov. 22, 2020, which is based upon and claims the priority of U.S. Provisional Patent Application Ser. No. 62/939,312, filed Nov. 22, 2019, and U.S. Provisional Patent Application Ser. No. 62/939,595, filed Nov. 23, 2019, each of which is incorporated herein by reference in its entirety.

FIELD

The present subject matter relates to systems and methods for manipulating and removing tissues. More particularly, the present subject matter relates to systems and methods for manipulating elevated tissues extending above a surface tissue.

BACKGROUND

Dissection and removal of tissues, for example tumors, tissues suspected to be tumors, like polyps, and the like, from a patient's organs, is a procedure known in the art. Dissection and removal of large, complex and distinct tissues is relatively easy and straightforward. However, dissection and removal of tissues that are slightly elevated from a surface of a tissue is more challenging, particularly when the elevated tissue to be removed resides in a cavity in the body. Manipulation of soft elevated tissues, as well as soft surface tissues, is more challenging, particularly when there is a desire to dissect and separate the elevated tissue by less invasive procedures, like endoscopic procedures, polypectomy, and the like. The dissection and separation of the elevated tissue is even more challenging when the elevated tissue to be removed is non-symmetric.

In addition, other types of manipulation of the elevated tissue are challenging, particularly when the elevated tissue is slightly elevated from the surface tissue. Some exemplary challenged manipulations include: close imaging of all the sides of the elevated tissue, injection of substances into all the sides of the elevated tissue, dissecting and ablation of all sides of the elevated tissue, for example by polypectomy and/or ablation and/or tissue disconnecting, a combination thereof and the like.

SUMMARY

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

According to one aspect of the present subject matter, there is provided a system for allowing controlled access of a tool to all sides of an elevated tissue in a body of a patient, the system comprising:

a rail configured to surround the elevated tissue; and
at least one vehicle configured to move along the rail and carry at least one tool configured to manipulate the elevated tissue.

According to one embodiment, at least one connector is attached to the vehicle, and configured to connect the at least one tool to the vehicle.

According to another embodiment, the rail is configured to be inserted into the body of the patient through an endoscope.

According to another embodiment, the at least one vehicle is configured to be inserted into the body of the patient through an endoscope.

According to yet another embodiment, the tool is a cutting tool comprising a blade configured to cut the elevated tissue.

According to still another embodiment, the system further comprises a manifold head configured to store the vehicle during transfer through the endoscope.

According to a further embodiment, the vehicle further comprises an imaging device.

According to yet a further embodiment, the vehicle further comprises at least one light source.

According to still a further embodiment, a vehicle cable is attached to the vehicle, and wherein movement of the vehicle along the rail is driven by pushing and pulling the vehicle cable.

According to an additional embodiment, the vehicle cable resides inside the rail.

According to yet an additional embodiment, the rail further comprises balls that are configured to be in contact with the vehicle cable and rotate when the vehicle cable is pushed or pulled, for facilitating smooth movement of the vehicle cable inside the rail.

According to still an additional embodiment, movement of the vehicle along the rail is driven manually.

According to another embodiment, the vehicle further comprises at least one bearing configured to roll over the rail and reduce friction forces exerted on the vehicle during the movement of the vehicle along the rail.

According to yet another embodiment, the vehicle further comprises a drive wheel configured to roll over the rail and drive the movement of the vehicle, and a motor configured to provide kinetic energy to the drive wheel.

According to still another embodiment, the rail is configured to assume any structure in any dimension, and adapt the structure of the rail to a contour and surface features of the elevated tissue that the rail surrounds, and a surface tissue on which the rail resides.

According to a further embodiment, the rail is elastic and flexible, and is further configured to become rigid as desired.

According to yet a further embodiment, a vehicle surface of the rail is toothed.

According to still a further embodiment, the vehicle comprise at least one toothed wheel configured to be in contact with and roll along the toothed vehicle surface.

According to an additional embodiment, a tissue surface of the rail is folded.

According to yet an additional embodiment, the rail comprises at least one suction pipe passing internally inside the rail, and at least one suction orifice on a tissue surface that is fluidically connected to the suction pipe, and wherein the suction pipe is configured to allow formation of negative gas pressure at the suction orifice in order to suck the elevated tissue that is in contact with the tissue surface and the at least one suction orifice on the tissue surface.

According to still an additional embodiment, the blade is configured to move in and out from the cutting tool.

According to another embodiment, the connector and the cutting tool are configured to turn left and right.

According to yet another embodiment, the connector and the cutting tool are configured to turn upward and downward.

According to still another embodiment, the imaging device is configured to change its orientation upwards and downwards relative to the vehicle.

According to a further embodiment, the system further comprising at least one control panel that is configured to control the operation of the system.

According to another aspect of the present subject matter, there is provided a method for cutting an elevated tissue in a body of a patient, the method comprising:
 inserting a rail to a vicinity of the elevated tissue;
 surrounding the elevated tissue with the rail;
 placing a vehicle on the rail;
 connecting a cutting device to the vehicle; and
 moving the vehicle along the rail while cutting the elevated tissue with the cutting device.

According to one embodiment, the inserting of the rail into the body of the patient is with an endoscope.

According to another embodiment, the cutting of the elevated tissue is controlled with a control panel operable through the endoscope.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

DESCRIPTION OF THE PREFERRED EMBODIMENTS

Figure 1:
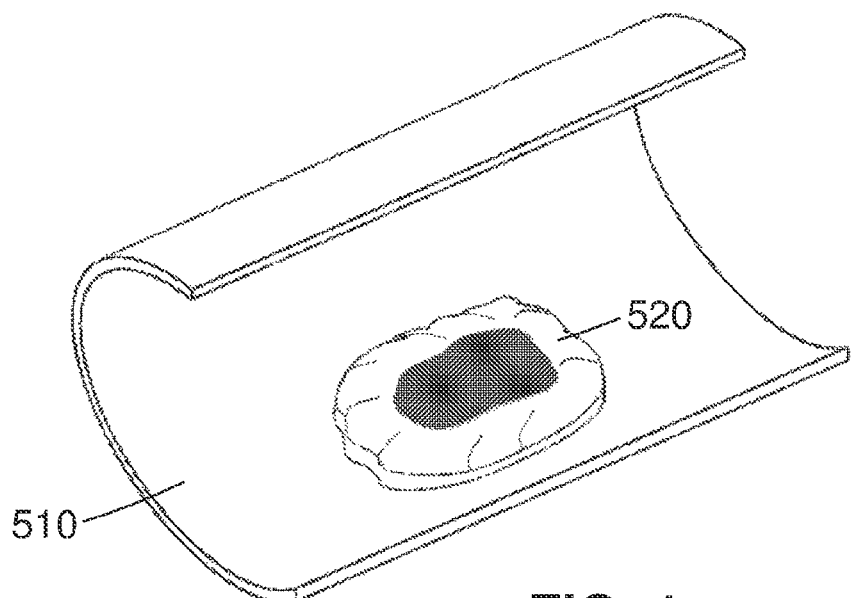
FIG. 1 schematically illustrates, according to an exemplary embodiment, a surface tissue, and an elevated tissue.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

Referring now to FIG. 1, schematically illustrating, according to an exemplary embodiment, a surface tissue, and an elevated tissue. FIG. 1 illustrates an elevated tissue 520 extending from a surface tissue 510. The surface tissue 510 is any type of tissue present in a body of a patient, for example a surface tissue 510 of an organ, or a cavity, in the body, like the colon, also known as the large intestine, as illustrated in FIG. 1, or any other type of tissue that can be accessed by any tool, for either surgical activity or any other manipulation.

The elevated tissue 520 is any type of tissue that is elevated from a surface tissue 510 and there is a desire to manipulate it, for example dissect and separate the elevated tissue 520 from the surface tissue 510, and in some embodiments, remove the dissected and separated elevated tissue 520 from the body of the patient; close imaging of all the sides of the elevated tissue 520 from appropriate angles; injection of substances into all the sides of the elevated tissue; burning all sides of the elevated tissue 520, a combination thereof, and the like. The use of the term "sides" is intended also to all the curves that form the shape of the elevated tissue 520.

Some exemplary elevated tissues 520 include: tumors, tissues suspected to be tumors, like polyps, lesions, a combination thereof, and the like. The elevated tissue 520 can be either symmetric, or non-symmetric. The elevated tissue 520 can be hard or soft. The elevated tissue 520 can be a large and distinct tissue that can be easily manipulated, for example dissected and separated from the surface tissue 510. Alternatively, the elevated tissue 520 can be slightly elevated from the surface tissue 510, rendering its manipulation more challenging.

The present subject matter provides a system and method for allowing access of a tool to all sides of an elevated tissue 520. Some exemplary tools that the system and method allow their access to all sides of the elevated tissue 520, include: a dissecting tool, a grabbing tool, an imaging tool, an injecting tool, a burning tool, and the like.

In some embodiments, the system and method of the present subject matter allow dissection and separation of an elevated tissue 520 from a surface tissue 510 in a body of a patient. In some other embodiments, the system and method of the present subject matter further allow removal of the dissected and separated elevated tissue 520 from the body of the patient. In some additional embodiments, the system and method of the present subject matter allow performance of additional manipulations on the elevated tissue 520 and its surroundings, as described in detail hereinafter.

According to one embodiment, the patient is an animal, particularly a vertebrate. According to another embodiment, the animal is a human.

The term "tool" as disclosed herein refers to any type of tool that is configured to be used during manipulation of tissues in a body of a patient. Some exemplary types of tools include; a dissecting tool configured to dissect a tissue; a grabbing tool configured to grab a piece of tissue; a storing tool configured to store an object, for example a piece of tissue, for example during removal of the object from the body of the patient; an imaging tool configured to acquire images inside a body of a patient; an illuminating tool configured to illuminate inside a body of a patient; an injecting tool configured to inject substances into a tissue; a burning tool configured to burn parts of a tissue, a combination thereof, and the like.

Figure 2:
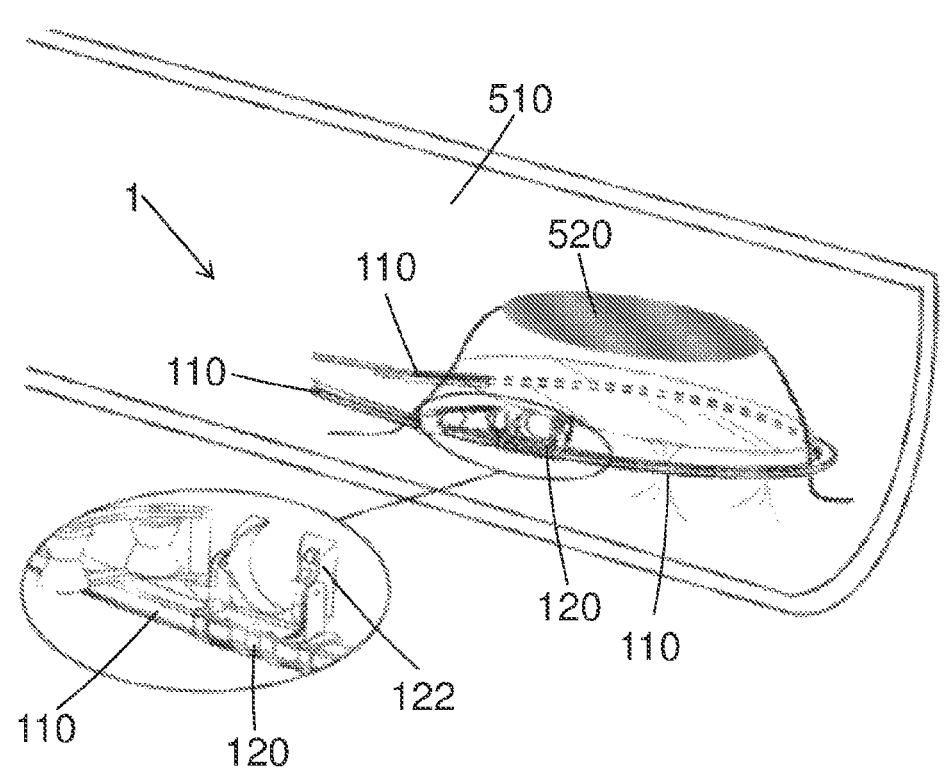
FIG. 2 schematically illustrates, according to an exemplary embodiment, a system for allowing controlled access of a tool to all sides of an elevated tissue in a body of a patient.

Referring now to FIG. 2, schematically illustrating, according to an exemplary embodiment, a system for allowing controlled access of a tool to all sides of an elevated tissue in a body of a patient. FIG. 2 illustrates components of a system 1 for allowing controlled access of a tool to all sides of an elevated tissue 520 in a body of a patient, the system 1 comprising:

a rail 110 configured to surround an elevated tissue 520 inside a body of a patient;

at least one vehicle 120 configured to move along the rail 110 and carry at least one tool configured to manipulate the elevated tissue.

According to one embodiment, at least one connector 122 is attached to the vehicle 120, and configured to connect the at least one tool to the vehicle 120.

According to one embodiment, the tool is an integral part of the vehicle 120. According to another embodiment, the tool is separated from the vehicle and configured to connect to the vehicle 120.

As can be seen in FIG. 2, the surface tissue 510 is apart of a cavity in a body of a patient, and the elevated tissue 520 extends from the surface tissue 510. The rail 110 surrounds the elevated tissue 520, and the vehicle 120 is stilled attached to, or moves along, the rail 110. Since the rail 110 surrounds the elevated target tissue 520, and the vehicle 120 is configured to move along the rail 110, the vehicle 120 can surround the elevated tissue 520. Thus, the system 1 allows access of the vehicle 120 to at least part of the elevated tissue 520, up to all sides of the elevated tissue 520, thereby allowing manipulation of the elevated tissue 520, depending on the tool connected to the vehicle 120.

Also illustrated in the circled zoom-in image in FIG. 2, at least one connector 122 attached to the vehicle 120. Thus, the system 1 allows access of any tool connected to the connector 122 to at least part of the elevated tissue 520, up to all sides of the elevated tissue 520 up to the edges of the elevated tissue.

According to one embodiment, the rail 110 and the vehicle 120 are configured to be inserted into a body of a patient. According to another embodiment, the rail 110 and the vehicle 120 are configured to be inserted into a cavity in the body of the patient. According to yet another embodiment, the rail 110 and the vehicle 120 are configured to be manually inserted into the body of the patient, or into a cavity in the body of the patient. According to a further embodiment, the rail 110 is configured to be inserted into the body of the patient, or into the cavity in the body of the patient, through an endoscope. According to yet a further embodiment, the vehicle 120 is configured to be inserted into the body of the patient, or into the cavity in the body of the patient, through an endoscope. According to still a further embodiment, the rail 110 and the vehicle 120 are both configured to be inserted into the body of the patient, or into the cavity in the body of the patient, through an endoscope. According to a further embodiment, the insertion of the rail 110, or the vehicle 120, or the rail 110 and the vehicle 120 can be either manual, or autonomous, namely by a robotic mechanism. According to an additional embodiment, the rail 110, or the vehicle 120, or both the rail 110 and the vehicle 120, are configured to be inserted in the body of the patient, or into the cavity in the body of the patient, through a multi-lumen that is transferred through an endoscope.

Figure 3:
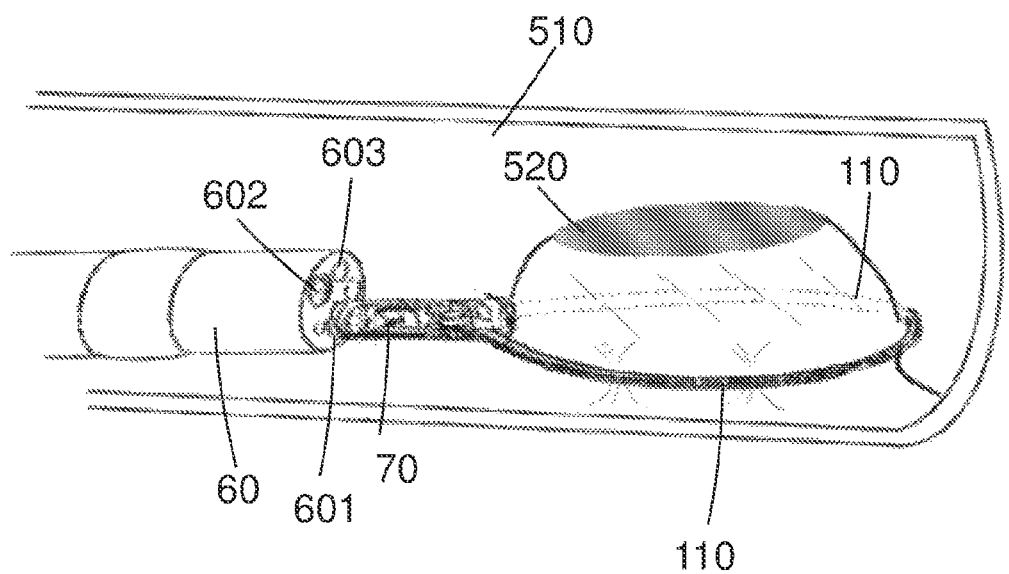
FIG. 3 schematically illustrates, according to an exemplary embodiment, a rail surrounding an elevated tissue, the rail protrudes from an endoscope inserted into a cavity of a body of a patient.

Referring now to FIG. 3, schematically illustrating, according to an exemplary embodiment, a rail surrounding an elevated tissue, the rail protrudes from an endoscope inserted into a cavity of a body of a patient. FIG. 3 illustrates an endoscope 60 that was inserted into a cavity of a body of a patient. Thus, the surface tissue 510 is the tissue of the cavity. As can be seen in FIG. 3, endoscope 60 has a tube-like structure. The endoscope 60 comprises at least one, but preferably a plurality of channels 601, 602, 603, through which objects, illumination, imaging, multi-lumen through which working tools such as a rail 110, a combination thereof and the like, can be transferred or positioned. Further seen in FIG. 3 is a rail 110 exiting a channel 601 of the endoscope 60 and surrounding an elevated tissue 520 extending above the surface tissue 510. In other words, FIG. 3 illustrates the exemplary embodiment of a rail 110 configured to be inserted into a body of a patient, or into a cavity in the body of the patient, through an endoscope, for example via a multi-lumen 70. In this embodiment, during insertion of the endoscope 60 into the body of the patient the rail 110 resides inside a channel 601 of the multi-lumen 70 that is inserted in an endoscope 60. When the endoscope 60 approaches a vicinity of the elevated tissue 520, the multi-lumen 70 can depart the endoscope, as seen in FIG. 4, and the rail 110 can exit the channel 601 in which the rail 110 resides, and surround the elevated tissue 520.

Figure 4:
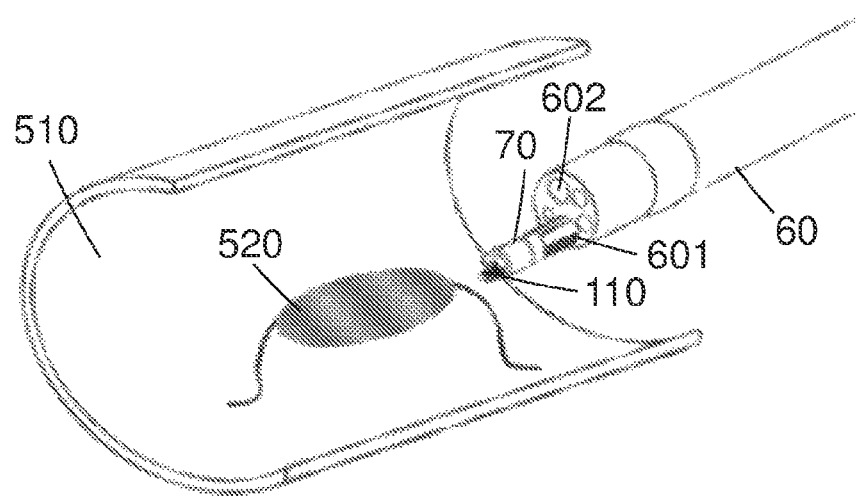
FIG. 4 schematically illustrates, according to an exemplary embodiment, a rail exiting a multi-lumen approaching an elevated tissue.

Referring now to FIG. 4, schematically illustrating, according to an exemplary embodiment, a rail exiting a multi-lumen approaching an elevated tissue. FIG. 4 illustrates an internal cavity having a surface tissue 510, and an elevated tissue 520 extending above the surface tissue 510. Also shown is a multi-lumen 70 that protrudes from the endoscope 60 and approaching to the vicinity of the elevated tissue 520. multi-lumen 70, during insertion of the endoscope into the cavity, the multi-lumen 70 resides inside the working channel 601 of the endoscope 60, and the rail 110 resides in the working channel 601 of the endoscope 60. When the endoscope approaches the vicinity of the elevated tissue 520, the multi-lumen 70 can extend out of the endoscope, and the rail 110 can exit from the channel 601 of the multi-lumen 70 towards the elevated tissue. FIG. 4 illustrates an edge of the rail 110 exiting the channel 601 of the endoscope 60. After the rail 110 exits the channel 601, the rail 110 is configured to surround the elevated tissue 520.

It should be noted again that the insertion of the rail 110 into the body to the vicinity of the elevated tissue 520, by using an endoscope, with or without a multi-lumen 70 in the endoscope, is only exemplary and should not be considered as limiting the scope of the present matter. The rail 110 can be brought to the vicinity of the elevated tissue 520 by any other mechanism as well, for example manually during an open surgery, or by any other means, for example a robotic arm, forceps, a combination thereof, and the like.

Figure 5:
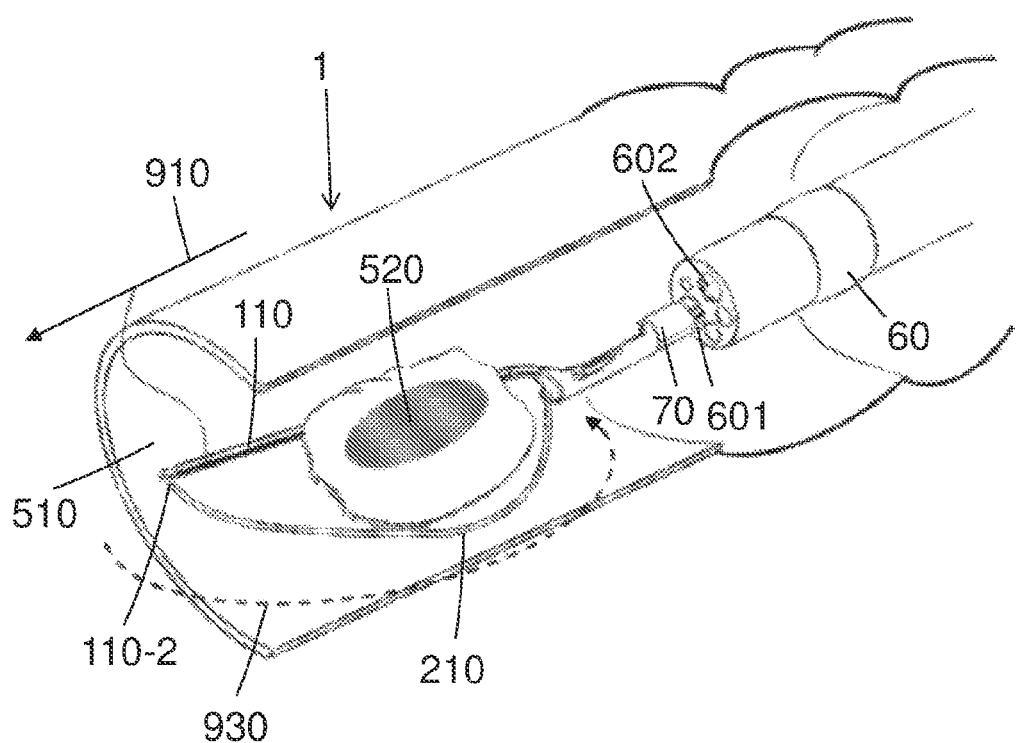
FIG. 5 schematically illustrates, according to an exemplary embodiment, a rail exiting a multi-lumen and surrounding an elevated tissue.

Referring now to FIG. 5, schematically illustrating, according to an exemplary embodiment, a rail exiting a multi-lumen and surrounding an elevated tissue. FIG. 5 illustrates an exemplary embodiment of a mechanism by which a rail 110 exiting a multi-lumen 70 surrounds an elevated tissue 520. According to one embodiment, the rail 110 comprises a distal edge 110-2. According to another embodiment, the system 1 further comprises a pulling element 210 is configured to be attached to the distal edge 110-2 of the rail 110. The pulling element 210 is also configured to reside inside a channel 601 of the multi-lumen 70. When the multi-lumen 70 reaches a vicinity of an elevated tissue 520, as shown in FIG. 4, the pushing element 210 that is attached to the distal edge 110-2 of the rail 110 is configured to exit the multi-lumen 70 alongside the rail 110. Then, rail 110 is configured to extend away from the multi-lumen 70, in a direction marked by arrow 910. According to one embodiment, as can be seen in FIG. 5, the rail 110 extends in a straight direction 910 from the multi-lumen 70. At this stage, the rail 110 itself is straight. Simultaneously, the pulling element 210 that is attached to the distal edge 110-2 of the rail 110, also exits the multi-lumen 70, and surrounds the elevated tissue 520 in an opposite side of the elevated tissue 520 compared to the rail 110. In order to allow the surrounding of the elevated tissue 520 by the rail 110, the pulling element 210 is pulled back into the multi-lumen 70 in direction 930, thus pulling the distal edge 110-2 of the rail 110 around the elevated tissue 520, and allowing the rail 110 to surround the elevated tissue 520. Eventually, the pulling element 210 is pulled back into the multi-lumen 70, and the rail 110 entirely surrounds the elevated tissue 520, as illustrated in FIG. 3. It should be noted that the rail 110 is configured to surround an elevated tissue 520 having any size, height and shape, including non-symmetrical elevated tissues 520. It should be noted also that the aforementioned mechanism and method of surrounding an elevated tissue 520 with the rail 110 is only exemplary, and should not be considered as limiting the scope of the present subject matter. Other mechanisms and methods of surrounding an elevated tissue 520 with the rail 110 are also under the scope of the present subject matter.

Figure 6:
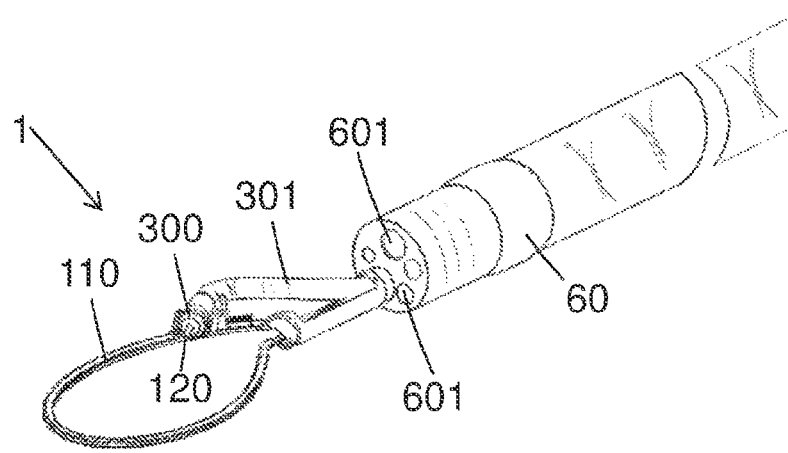
FIG. 6 schematically illustrates, according to an exemplary embodiment, a rail in a surrounding position extending from a multi-lumen, and a vehicle standing or moving on the rail.

Referring now to FIG. 6, schematically illustrating, according to an exemplary embodiment, a rail in a surrounding position extending from a multi-lumen, and a vehicle standing or moving on the rail. FIG. 6 illustrates the aforementioned embodiment, according to which, the vehicle 120 is configured to be inserted into the body of the patient, or into the cavity in the body of the patient, through a multi-lumen 70 that is transferred through an endoscope. As can be seen in FIG. 6, a tool 300 is attached to the vehicle 120. The tool 300 can also be connected to a cable 301. The cable 301 runs through a channel 601 of the multi-lumen 70 and the endoscope, to a control panel operated by an operator, as will be shown in other drawings hereinafter.

Figure 7:
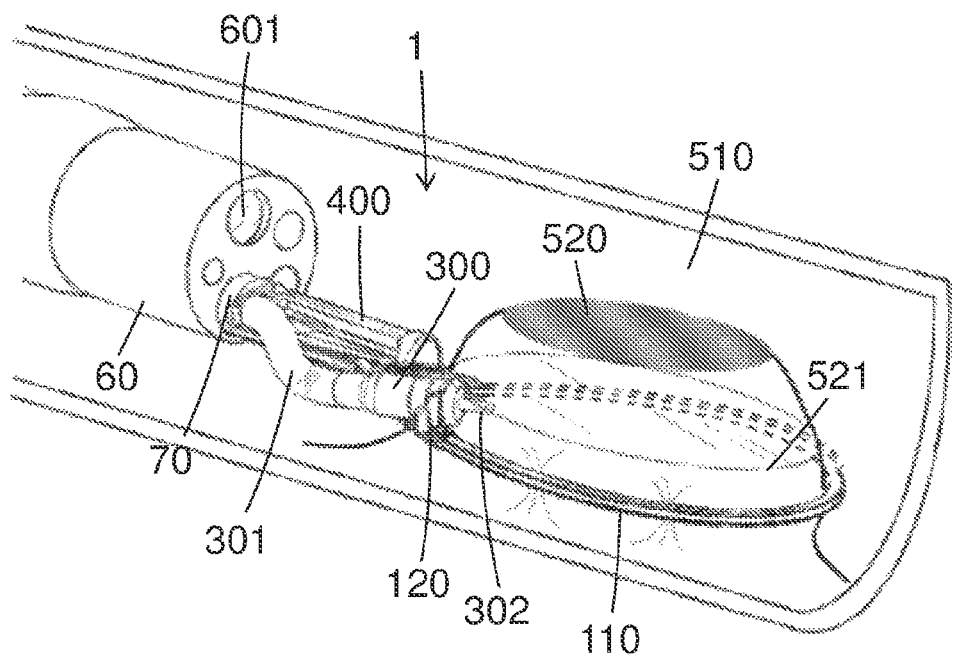
FIG. 7 schematically illustrates, according to an exemplary embodiment, a rail surrounding an elevated tissue, a vehicle standing or moving along the rail, and a tool attached to the vehicle.

Referring now to FIG. 7, schematically illustrating, according to an exemplary embodiment, a rail surrounding an elevated tissue, a vehicle standing or moving along the rail, and a tool attached to the vehicle. FIG. 7 is similar to FIG. 6, except that FIG. 7 shows the elevated tissue 520 that is surrounded by the rail 110. As mentioned above, the rail 110 that surrounds the elevated tissue 520 allows movement of the vehicle 120 around the elevated tissue 520. FIG. 7 shows the vehicle 120 standing or moving along the rail 110, and a tool 300 attached to the vehicle 120, and a cable 301 attached to the tool 300 and passing though the multi-lumen 70. The tool 300 shown in FIG. 7 is a cutting tool 300 that is configured to cut the elevated tissue 520. The cutting tool 300 comprises a blade 302 configured to cut the elevated tissue 520. Any mechanism by which the blade 302 is configured to cut the elevated tissue 520 is under the scope of the present subject matter, for example by heating the elevated tissue. According to one embodiment, the blade 302 cuts the elevated tissue 520 during movement of the vehicle 120 on the rail 110. A cut line 521 over the elevated tissue 520 designates a line on which the elevated tissue 520 is cut during movement of the blade 302 along the elevated tissue 520 as a result of the movement of the vehicle 120 along the rail 110. Three-dimensionally, the cut line 521 defines a plane of cut of the elevated tissue 520. In some embodiments, the plane of cut of the elevated tissue is parallel to a base of the elevated tissue 520. The cut line 521 can be planned before the procedure of cutting the elevated tissue 520 with the system 1 so that the procedure can be controlled.

Additionally, seen in FIG. 7 is a manifold head 400 configured to store the vehicle 110 during transfer through from the multi-lumen 70. After the rail 110 is positioned in place around the elevated tissue 520, the vehicle 110 exists the manifold head 400 to the rail 110 and can start its working mode.

Figure 8:
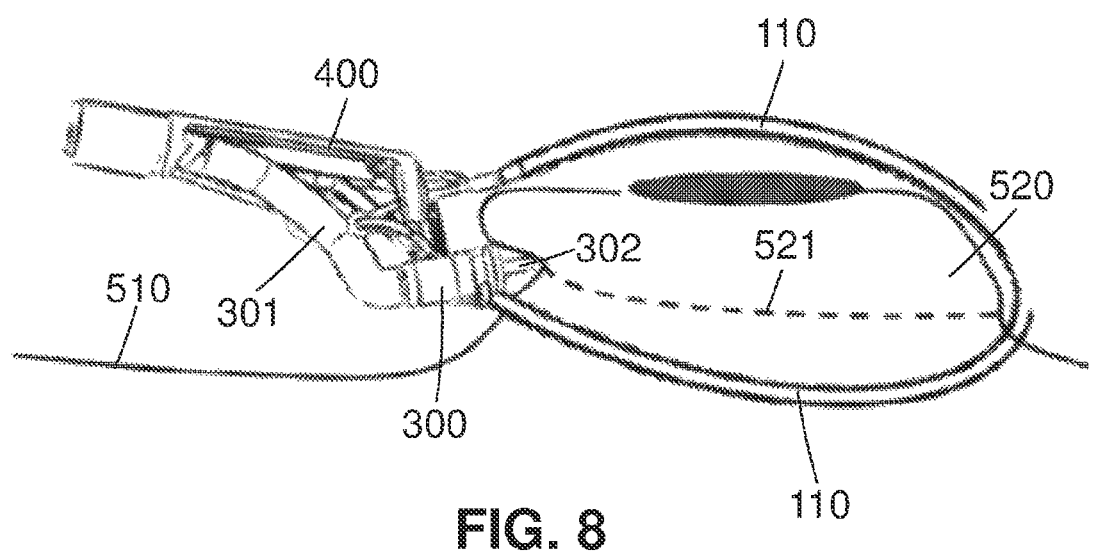
FIG. 8 schematically illustrates, according to an exemplary embodiment, another view of a rail surrounding an elevated tissue, a vehicle standing or moving along the rail, and a tool attached to the vehicle.

Referring now to FIG. 8, schematically illustrating, according to an exemplary embodiment, another view of a rail surrounding an elevated tissue, a vehicle standing or moving along the rail, and a tool attached to the vehicle. The features illustrated in FIG. 8 are similar to the feature illustrated in FIG. 7. However, FIG. 8 provides another view of the manifold head 400. Using this view, it is clearer that the manifold head 400 can have a corner-like shape and provides a shelter to the vehicle 110 during transfer through the endoscope and the multi-lumen 70.

Figure 9:
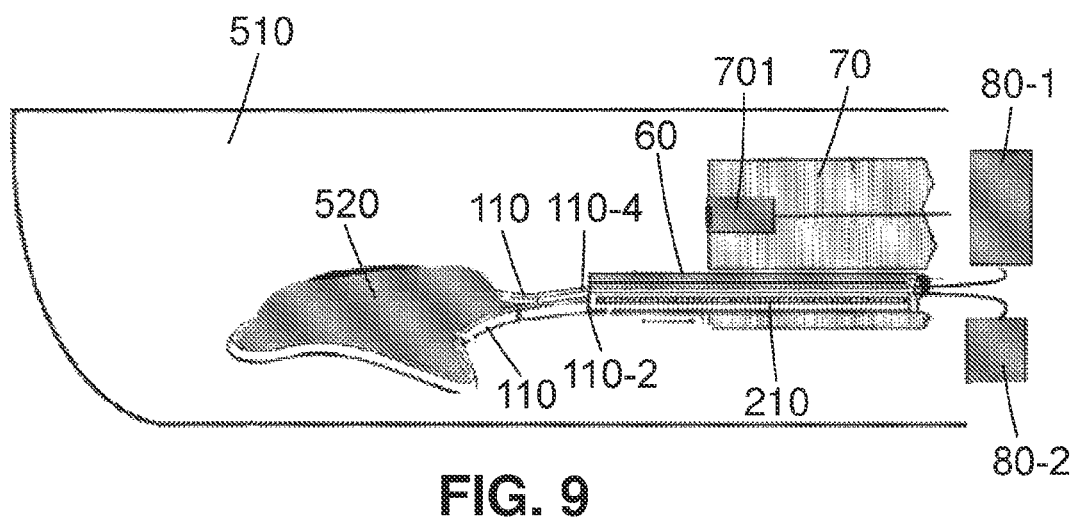
FIG. 9 schematically illustrates, according to an exemplary embodiment, an overall view of the system.

Referring now to FIG. 9, schematically illustrating, according to an exemplary embodiment, an overall view of the system. FIG. 9 illustrates some additional embodiments of the system. The endoscope 70 is seen, comprising an endoscope camera 602. The multi-lumen 70 resides in the endoscope 60, while in the vicinity of the elevated tissue 520, the multi-lumen 70 extends out of the endoscope 60. The rail 110 protrudes from the multi-lumen 70, surrounds the elevated tissue 520 and returns to the multi-lumen 70. The rail 110 has a distal edge 110-2, also shown in FIG. 5. The distal edge 110-2 is movable. Namely, the distal edge 110-2 of the rail exits the multi-lumen 70, surrounds the elevated tissue 520, and returns to the multi-lumen 70. An opposite edge of the rail 110 is referred to as a proximal edge 110-4 of the rail 110. The proximal edge 110-4 remains inside the multi-lumen 70 during deployment of the rail 110 around the elevated tissue 520. Therefore, the proximal edge 110-4 of the rail is also referred to as the fixed edge 110-4 of the rail 110.

Also seen in FIG. 9 is the pulling element 210 attached to the distal edge 110-2 of the rail 110. An operator of the system 1 can pull the pulling element 210 in order to tighten the embrace of the elevated tissue 520 by the rail 110. Alternatively, the pulling element can be pushed in a direction outside the multi-lumen 70 in order to release the embrace of the elevated tissue 520 by the rail 110.

The system 1 further comprises at least one control panel 80. FIG. 9 illustrates an embodiment of the system 1 comprising two control panels 80—a first control panel 80-1 and a second control panel 80-2. The at least one control panel 80 is configured to allow an at least one, preferably two, operators of the system 1 to operate the system 1 and control the action of the various components of the system 1, for example, the rail 110, the vehicle 120, the tool 300, the endoscope 60, the multi-lumen 70, the endoscope camera 602, and additional components described herein. For example, the pulling element 210 is attached to a control panel 80, and the operator can push or pull the pulling element 210 as desired mechanically, electronically, magnetically, a combination thereof and the like.

Figure 10:
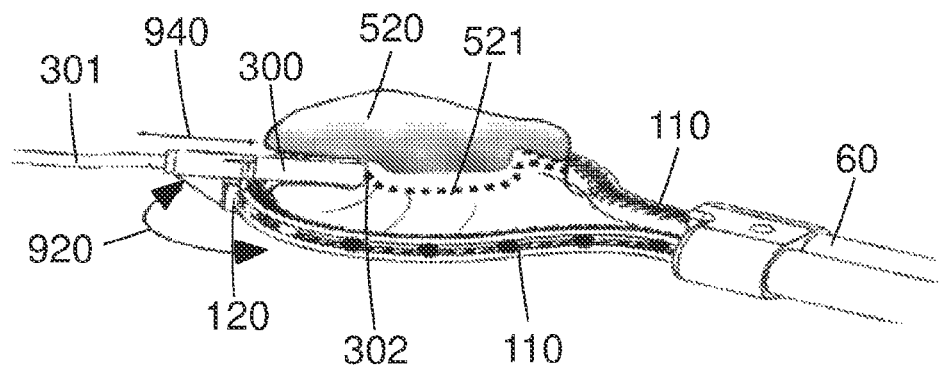
FIG. 10 schematically illustrates, according to an exemplary embodiment, a rail surrounding an elevated tissue and a cutting tool attached to a vehicle moving along the rail, while the cutting tool cuts the elevated tissue.

Referring now to FIG. 10, schematically illustrating, according to an exemplary embodiment, a rail surrounding an elevated tissue and a cutting tool attached to a vehicle moving along the rail, while the cutting tool cuts the elevated tissue. FIG. 10 shows a rail 110 exiting a multi-lumen 70, surrounding an elevated tissue 520, and returning to the multi-lumen 70. A vehicle 120 moves along the rail 110 in a circular direction 920 according to the route of the rail 110. The circular arrow 920 that designates the direction of movement of the vehicle 120 is bi-directional, indicating that the vehicle 120 can move along the rail in both possible directions, for example forward and backward. A cutting tool 300 is attached to the vehicle 120, and a cable 301 is attached to the cutting tool 300. The cable 301 is connected to a control panel 80, and passes through the endoscope 60, or the multi-lumen 70 as well, thus allowing control of the operation of the cutting tool 300 by the operator. During the movement of the vehicle 120 on the rail 110, the blade 302 cuts the elevated tissue 520 along a cut line 521 that can be pre-determined prior to this procedure. According to some embodiments, the cutting of the elevated tissue 520 is gradual. In other words, during a travel of the vehicle 120 around the elevated tissue 520, the blade 302 cuts the elevated tissue 520 in a certain depth in the elevated tissue 520. Then, during a following travel of the vehicle 120 along the rail 110, the blade further extends from the cutting tool 300 and cuts further inside the elevated tissue. Thus, during the cutting process, the blade 302 can extend out of the cutting tool 300 and back into the cutting tool, in a straight direction designated with a bidirectional arrow straight arrow 940.

Figure 11:
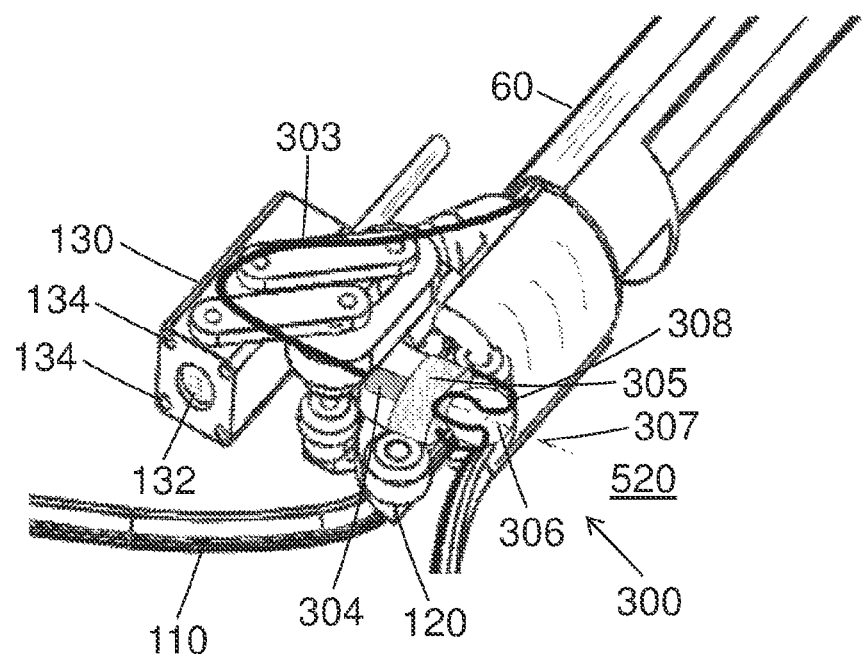
FIG. 11 schematically illustrates, according to an exemplary embodiment, a cutting tool comprising a laser blade, attached to a vehicle.

Referring now to FIG. 11, schematically illustrating, according to an exemplary embodiment, a cutting tool comprising a laser blade, attached to a vehicle. FIG. 11 illustrates an additional embodiment of a blade of a cutting tool 300—a laser blade. The laser blade comprises an optical fiber 303 running from the control panel 80, seen in FIG. 9, through the endoscope 60, and optionally through the multi-lumen 70, toward the cutting tool 300. A distal fiber edge 304 of the optical fiber 303 is attached to a lens 305, and a spherical transparent medium 306 is held in contact with the lens 305. The optical fiber 303 is configured to allow passage of a laser beam through the optical fiber 303. The lens 305 is configured to focus the laser beam and direct the focused laser beam toward the spherical transparent medium 306. The spherical transparent medium 306 is configured to allow passage of the focused laser beam toward a tissue 520 to be cut by the focused laser beam, for example an elevated tissue 520. Line 307 shows the direction of the focused laser beam passing through the spherical transparent medium 306. The spherical transparent medium 306 is also configured to prevent passage of the focused laser beam through the air. Therefore, the spherical transparent medium is always in contact with the lens 305 and the tissue 520 to be cut by the focused laser beam. Therefore, the spherical transparent medium 306 is spherical, in order to allow turning and sliding of the spherical transparent medium 306 over the tissue 520 to be cut during movement of the vehicle 120. This embodiment is achieved by a holder 308 configured to hold the spherical transparent medium 306 and maintain continuous contact of the spherical transparent medium 306 with the lens 305 and the tissue 520 to be cut. Any shape of the holder 308 is under the scope of the present subject matter, for example a holder 308 having a spiral line shape, as shown in FIG. 11.

FIG. 11 further shows the vehicle 120 to which the laser blade is attached, and the rail 120 on which the vehicle 120 moves. Also shown is the multi-lumen 70 through which the components are transferred.

Additionally, shown in FIG. 11 is an imaging device 130, for example a camera 130, attached to the vehicle 110. The imaging device 130 comprises an imaging device lens 132, that can comprise at least one light source 134, for example a light emitting diode, also known as LED, configured to illuminate an area that is imaged, or photographed, by the imaging device 130. Preferably, the number of light sources 304 is even, for example four as can be seen in FIG. 11, in order to achieve symmetric illumination of the area that is imaged or photographed.

Figure 12:
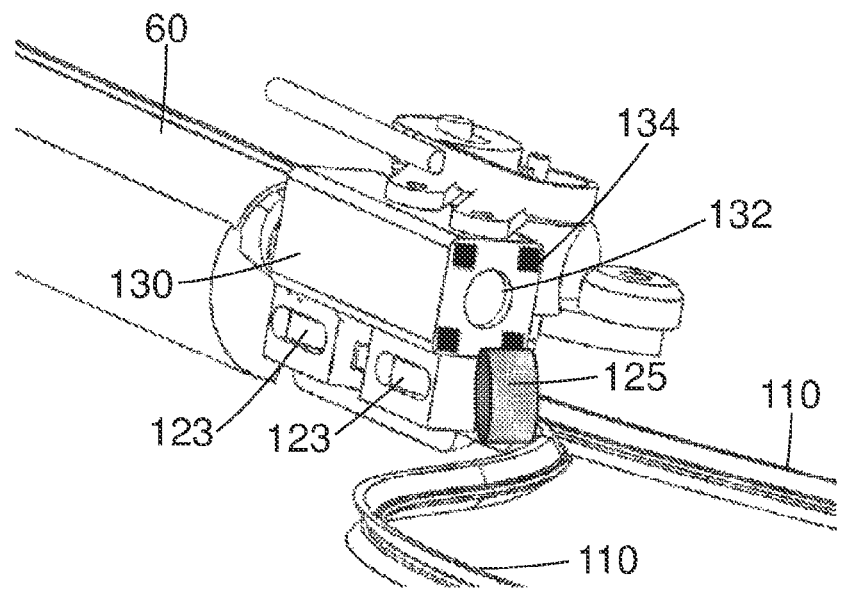
FIG. 12 schematically illustrates, according to an exemplary embodiment, a vehicle comprising at least one bearing and at least one drive wheel.

Referring now to FIG. 12, schematically illustrating, according to an exemplary embodiment, a vehicle comprising at least one bearing and at least one drive wheel. According to one embodiment, the vehicle 120 can move along the rail 110 by pushing and pulling the vehicle 120 with a cable that is attached to the vehicle 120, optionally passes through the multi-lumen 70 and the endoscope 60. The cable can continue till a control panel 80, similarly to the cable 301 illustrated in FIG. 9. According to another embodiment, the vehicle 120 can comprise at least one bearing 123 configured to roll over the rail 110 and reduce friction forces exerted on the vehicle 120 during the movement of the vehicle 120 along the rail. This at least one bearing 123 is illustrated in FIG. 12.

According to another embodiment, illustrated in FIG. 12, the vehicle 120 comprises a drive wheel 125 configured to roll over the rail 110 and drive the movement of the vehicle 120. This embodiment renders the vehicle 120 the autonomous ability to drive the vehicle 120 along the rail 110. The vehicle 120 illustrated in FIG. 12 further comprises an internal motor (not seen) that is configured to provide kinetic energy to the drive wheel 125.

Figure 13:
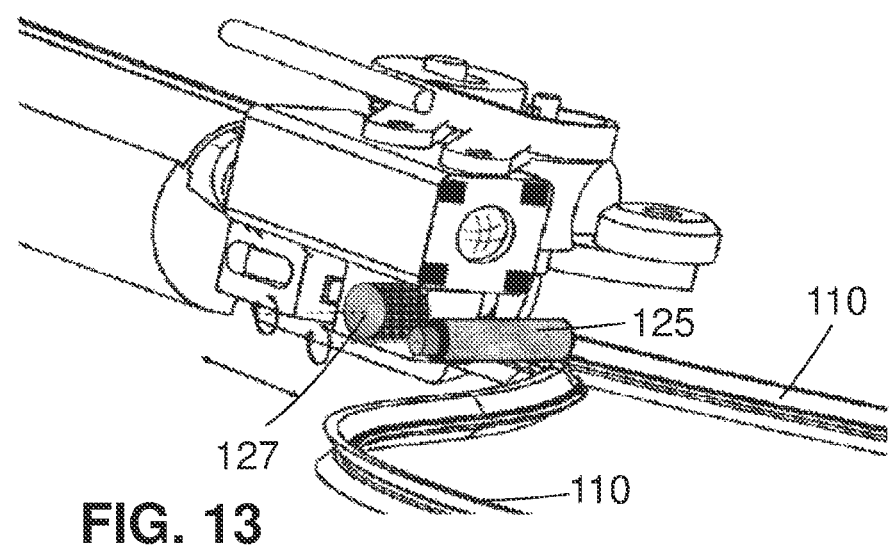
FIG. 13 schematically illustrates, according to an exemplary embodiment, a vehicle further comprising an external motor.

Referring now to FIG. 13, schematically illustrating, according to an exemplary embodiment, a vehicle further comprising an external motor. In another embodiment, the aforementioned motor 127 is external, and can be seen in FIG. 13.

Figure 14:
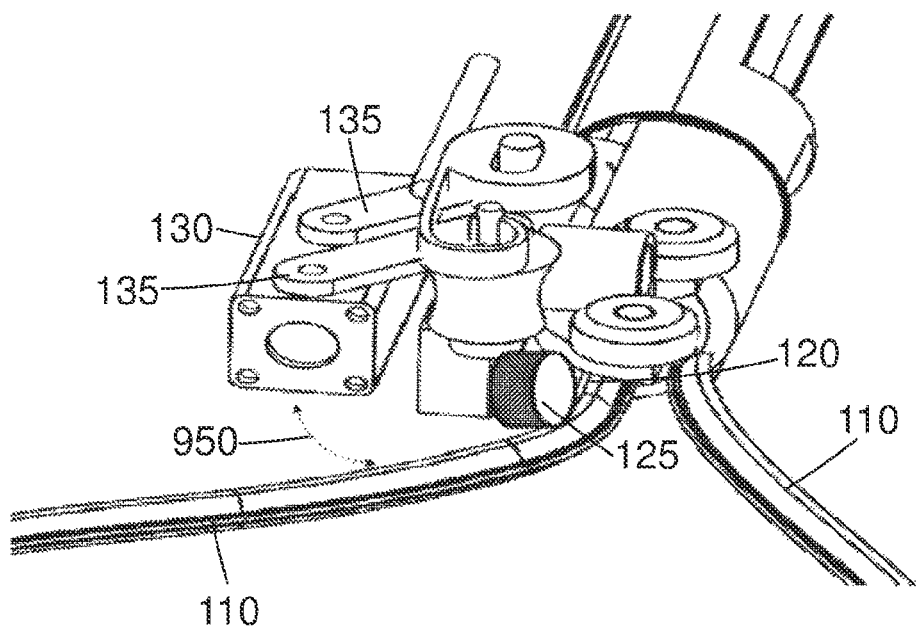
FIG. 14 schematically illustrates, according to an exemplary embodiment, another view of a vehicle comprising a drive wheel.

Referring now to FIG. 14, schematically illustrating, according to an exemplary embodiment, another view of a vehicle comprising a drive wheel. FIG. 14 shows a different view of the same embodiments illustrated in FIGS. 12 and 13. It is clearly seen in FIG. 14 that the drive wheel 125 is configured to attach the rail 110 while rotating, in order to drive the movement of the vehicle 120 along the rail 110.

An additional embodiment seen in FIG. 14 relates to the imaging device 130. According to one embodiment, the imaging device 130 is configured to change its orientation upwards and downwards relative to the vehicle 120, as illustrated with the bidirectional curved arrow 950. This can be achieved, for example, by using at least one arm 135, for example two arms 135 as shown in FIG. 14, that is connected to the imaging device 130 and the vehicle 120, and configured to change the orientation of the imaging device 130 upwards and downwards relative to the vehicle 120.

Returning now to FIG. 6. As can be seen in FIG. 6, the rail 110 is configured to bend and form a loop-like structure when deployed outside the endoscope 60, or the multi-lumen 70. In other words, the rail 110 is configured to exit the endoscope 60, or the multi-lumen 70, turn and return to the endoscope 60, or multi-lumen 70, while assuming a loop-like structure, as shown in FIG. 6.

Returning now to FIG. 9. The rail 110 shown in FIG. 9 surround an elevated tissue 520 and assumes the structure of the contour of the elevated tissue 520 in the place where the rail 110 surrounds the elevated tissue 520. As can be seen in FIG. 9, the contour of the elevated tissue is amorphic, but nevertheless the rail 110 is configured to assume even an amorphic structure that relates to the structure of the contour of the elevated tissue 520. In other words, the rail 110 is configured to assume any two-dimensional structure over a planar surface.

Figure 15:
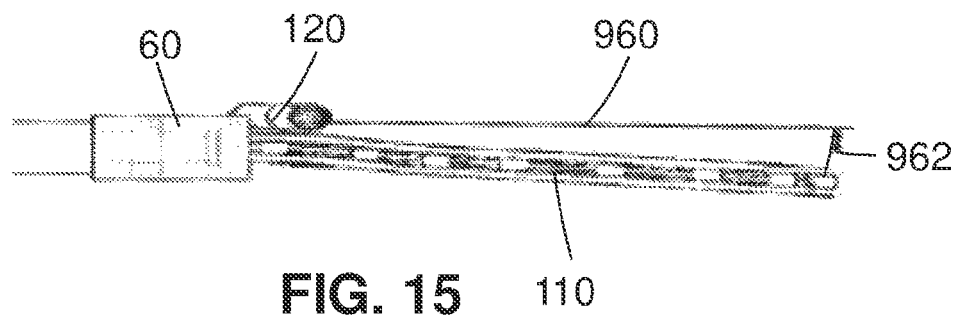
FIG. 15 schematically illustrates, according to an exemplary embodiment, a side view of a rail extended from a multi-lumen.

Referring now to FIG. 15, schematically illustrating, according to an exemplary embodiment, a side view of a rail extended from a multi-lumen. FIG. 15 shows a side view of a rail 110 extending from a multi-lumen 70 and a vehicle 120 standing still on the rail 110. Line 960 is a horizontal line exiting the multi-lumen. As can be seen in FIG. 15, the rail 110 is bent downwards relative to the horizontal line 960, and forming an angle 962 between the rail 110 and the horizontal line 960. This shows that the rail 110 is configured to bend up and down relative to a horizontal plane. It should be noted that similarly to the bending downwards relative to the horizontal line 960, the rail 110 is configured to bend upwards relative to the horizontal line 960. This embodiment allows the rail 110 to assume any contour structure of the surface tissue 510 on which the rail 110 resides, up and down relative to a horizontal line 960.

To summarize, the rail 110 is configured to assume any structure in any dimension, and adapt the structure of the rail 110 to the contour and surface features of the elevated tissue 520 that the rail surrounds, and the surface tissue 510 on which the rail resides. This embodiment can be achieved due to an elasticity, and flexibility of the rail 110.

Figure 16:
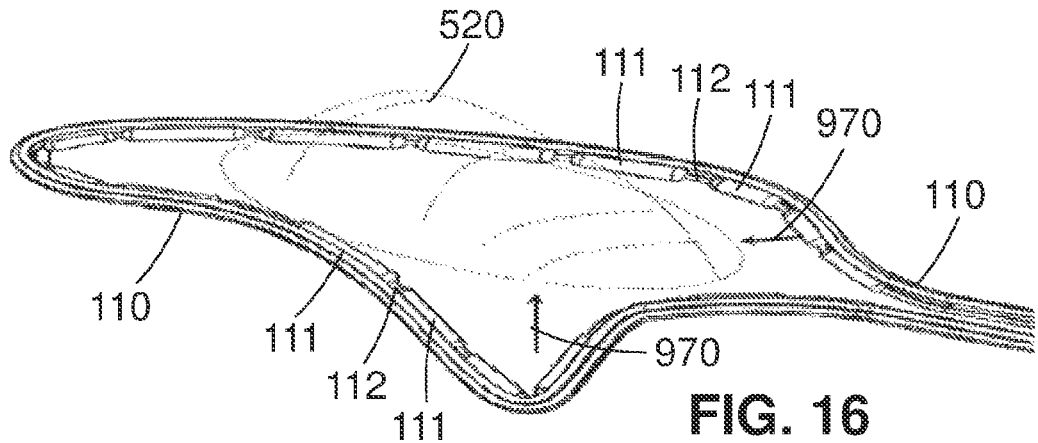
FIG. 16 schematically illustrates, according to an exemplary embodiment, a rail comprising inflatable elements surrounding an elevated tissue.

Referring now to FIG. 16, schematically illustrating, according to an exemplary embodiment, a rail comprising inflatable elements surrounding an elevated tissue. FIG. 16 shows a rail 110 surrounding an elevated tissue 520. In order to achieve that structure of the contour of the elevated tissue 520, parts of the rail 110 have to move toward the elevated tissue as shown for example by arrows 970 for some parts of the rail 110. This can be achieved due to the elasticity, and flexibility of the rail 110.

After the rail 110 has assumed a desired structure, in order to allow movement of the vehicle 120 along the rail 110, in some occasions there is a need for the rail 110 to become rigid, because in some embodiments of the rail 110 and the vehicle 120 the vehicle cannot move along an elastic, or flexible rail 110. One of the mechanisms to make the rail 110 or parts of it rigid, for example after the rail has assumed a desired structure, is shown in FIG. 16. According to this embodiment, the rail 110 comprises multiple inflating elements 111 that are attached along the rail 110 and configured to be inflated. Therefore, the inflatable elements 111 are connected to at least one pipe 112 that transfers a fluid to the inflating elements 111, and is also configured to transfer the fluid from the inflatable elements 111, for example in order to empty the fluid from the inflatable elements 111 and let the rail 110 to regain its elasticity and flexibility. For this purpose, the at least one pipe 112 passes through the rail 110 to the inflatable elements 111, and from the rail 110, through the endoscope 60, and occasionally through the multi-lumen 70, to a control panel 80. Any type of fluid is suitable for inflating the inflatable elements 111, for example a gas like air, nitrogen, carbon dioxide, and the like; or a liquid like water, saline, oil, and the like.

Figure 17:
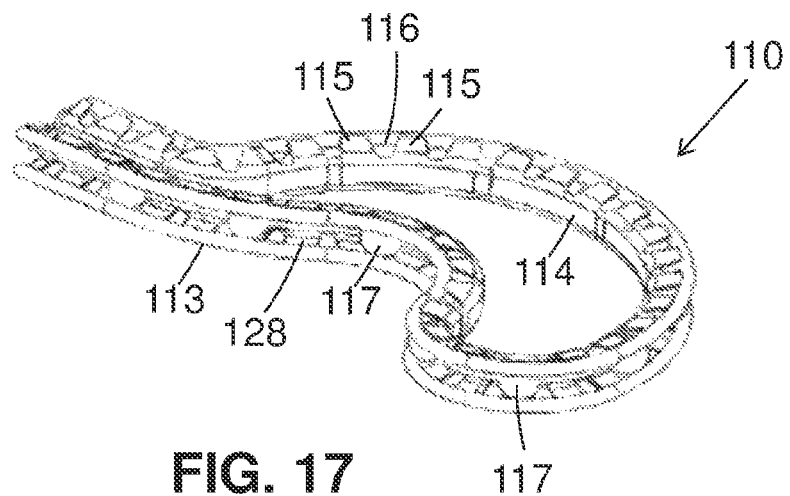
FIG. 17 schematically illustrates, according to an exemplary embodiment, a vehicle surface and a tissue surface of a rail.

Referring now to FIG. 17, schematically illustrating, according to an exemplary embodiment, a vehicle surface and a tissue surface of a rail. According to one embodiment, the rail 110 comprises a vehicle surface 113 along the rail 110, and a tissue surface 114 along the rail 110. The vehicle surface 113 is configured to face a vehicle 120 that stands on or moves along the rail 110, and in some embodiments, the vehicle surface 113 is also configured to be in contact with the vehicle 120 that stands on or moves along the rail 110. The tissue surface 114 is configured to be in contact with the elevated tissue 520 that is surrounded by the rail 110.

FIG. 17 further illustrates an exemplary embodiment of the structure of the vehicle surface 113, and a mechanism for moving the vehicle along the rail 110. In this embodiment, the rail 110 comprises a flat tissue surface 114 and a plurality of extensions 115, having gaps 116 in between the extensions 115, protruding substantially vertically to the tissue surface 114 and away from the tissue surface 114, from an upper side and a lower side of the tissue surface 114, thus forming a groove-like structure of the vehicle surface 113 having slotted walls comprised of the extensions 115 and the gaps 116 in between them. This structure of the slotted walls confers flexibility to the rail 110 and facilitates bending of the rail 110 when assuming a desired structure or contour. The groove-like structure of the vehicle surface 113 is configured to accommodate vehicle cable 128 that is attached to the vehicle 120, passes along the rail 110 through the endoscope 60, and optionally though the multi-lumen 70, until a control panel 80. The vehicle 120 is moved by pushing and pulling the vehicle cable 128. In order to facilitate smooth movement of the vehicle cable 128, the rail 110 can further comprise a plurality of balls 117 trapped in the groove-like structure of the vehicle surface 113 along the rail 110, the balls 117 are configured to be in contact with the vehicle cable 128 and rotate when the vehicle cable 128 is pushed or pulled.

Figure 18:
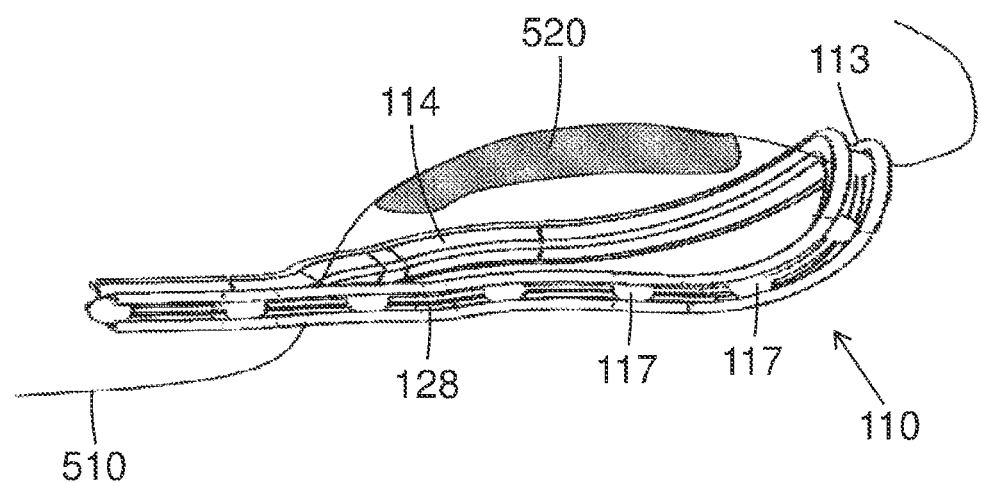
FIG. 18 schematically illustrates, according to an exemplary embodiment, an elevated tissue surrounded by a rail comprising a vehicle cable and a plurality of balls.

Referring now to FIG. 18, schematically illustrating, according to an exemplary embodiment, an elevated tissue surrounded by a rail comprising a vehicle cable and a plurality of balls. FIG. 18 illustrates a rail 110 that similarly to the rail 110 shown in FIG. 17 comprises a vehicle cable 128 and a plurality of balls 117 for facilitating smooth movement of the vehicle cable 128. The rail 110 illustrated in FIG. 18 also comprises a vehicle surface 113 having a groove-like structure that is configured to trap the balls 117 along the rail 110. However, in contrast to the rail 110 illustrated in FIG. 17, in which the walls of the groove-like structure are slotted and made of extensions 115 and gaps 116 in between the extension, the walls of the groove-like structure of the vehicle surface 113 shown in FIG. 18 are complete or full, not slotted. Therefore, the walls of the vehicle surface 113 of the rail 110 shown in FIG. 18 are made of an elastic or flexible material in order to allow the rail 110 to assume any desired structure according to the contour of the elevated tissue 520 that has to be surrounded by the rail 110, as can be seen in FIG. 18. It can be seen that the elevated tissue 520 is elevated above the surface tissue 510, and that the tissue surface 114 is in contact with the elevated tissue 520.

Figure 19:
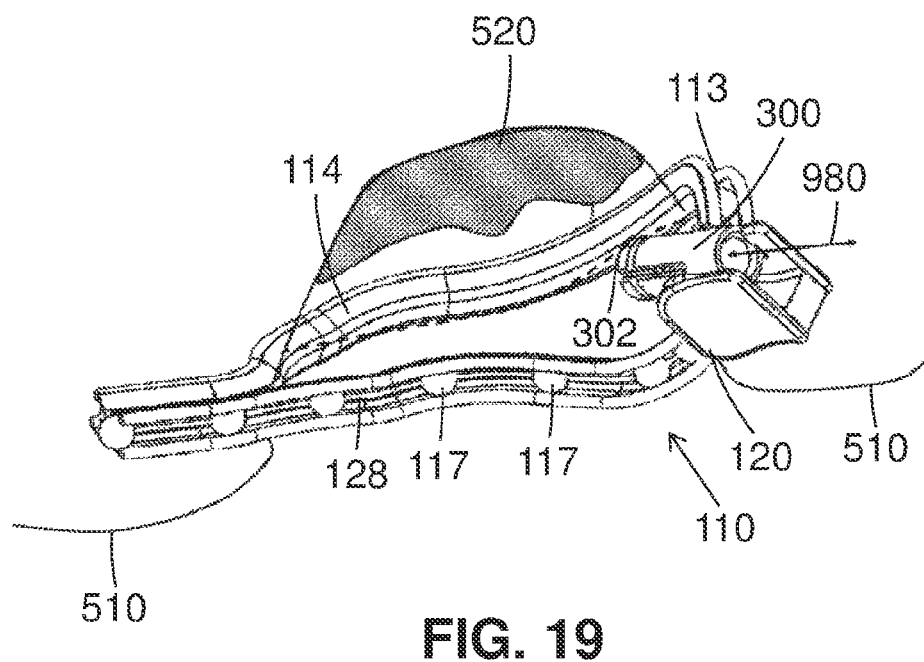
FIG. 19 schematically illustrates, according to an exemplary embodiment, an elevated tissue surrounded by a rail comprising a vehicle cable and a plurality of balls, and a vehicle with a cutting tool moving along the rail.

Referring now to FIG. 19, schematically illustrating, according to an exemplary embodiment, an elevated tissue surrounded by a rail comprising a vehicle cable and a plurality of balls, and a vehicle with a cutting tool moving along the rail. It should be noted that the elevated tissue 520 shown in FIGS. 18 and 19 is illustrated as transparent. Therefore, the tissue surface 114 of the rail 110 that is attached to a rear surface of the elevated tissue 520 can be seen through the so-called transparent elevated tissue 520. The rail 110 shown in FIG. 19 is similar to the rail 110 shown in FIG. 18. FIG. 19 shows, in addition, a vehicle 120 on the vehicle surface 113 of the rail 110. As described above, the vehicle cable 128 that passes along the groove-like structure of the vehicle surface 113 is attached to the vehicle 120, for allowing driving the movement of the vehicle 120 along the rail 110 by pushing and pulling the vehicle cable 128 from control panel 80. Also shown in FIG.

19 is a cutting tool 300 attached to the vehicle 120 that cuts the elevated tissue 520 during the movement of the vehicle 120.

In addition to the aforementioned embodiments, FIG. 19 also shows a direction of movement of the cutting tool 300, and additionally and more specifically of the blade 302 of the cutting tool 300. According to one embodiment, the cutting tool 300 is configured to move in the direction of the elevated tissue 520 and away from the elevated tissue 520, as designated with arrow 980 in FIG. 19. This embodiment is important for the cutting process of the elevated tissue 820 during movement of the vehicle 120, and the cutting tool 900 that is attached to the vehicle 120, along the rail 110. This embodiment can allow control of the depth of cutting in the elevated tissue 520. When the cutting tool 300, the blade 302, or both the cutting tool 300 and the blade 302, move toward the elevated tissue 520—this increases the depth of cutting of the elevated tissue 520, and vice versa.

Figure 20:
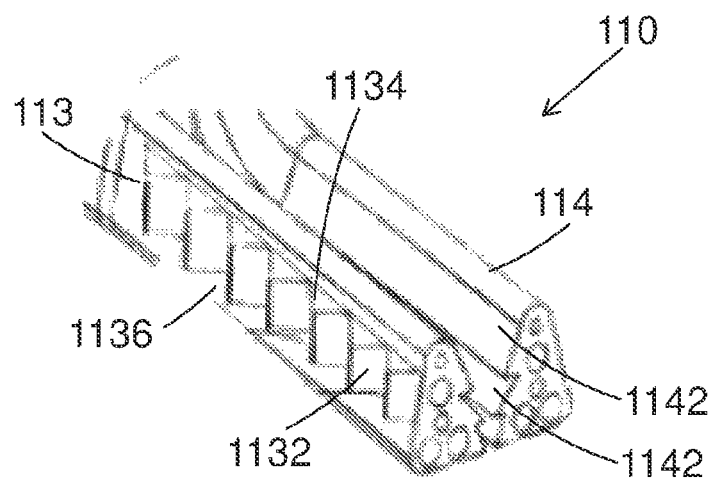
FIG. 20 schematically illustrates, according to an exemplary embodiment, a segment of rail having a toothed vehicle surface and a folded tissue surface.
Figure 21:
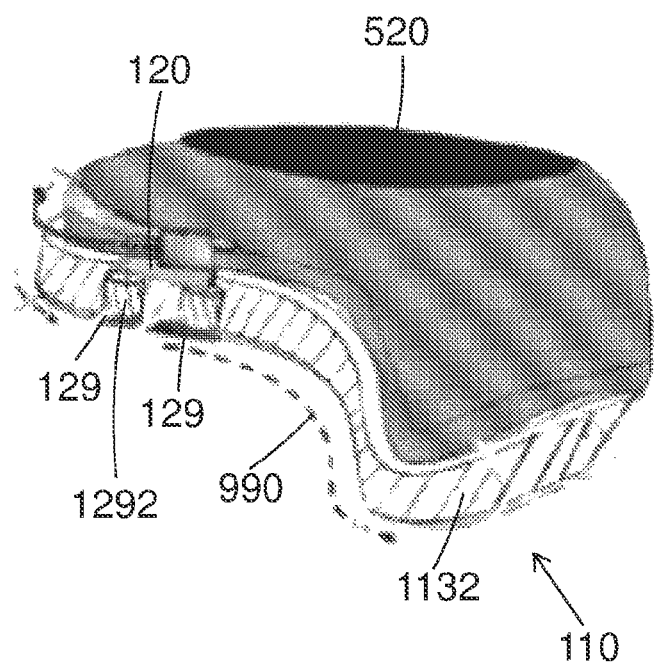
FIG. 21 schematically illustrates, according to an exemplary embodiment, the rail shown in FIG. 20 surrounding an elevated tissue and a vehicle with a cutting tool moving along the rail.

Referring now to FIG. 20, schematically illustrating, according to an exemplary embodiment, a segment of rail having a toothed vehicle surface and a folded tissue surface; and to FIG. 21, schematically illustrating, according to an exemplary embodiment, the rail shown in FIG. 20 surrounding an elevated tissue and a vehicle with a cutting tool moving along the rail. FIG. 20 shows an embodiment of a toothed vehicle surface 113 of the rail 110, and an embodiment of a folded tissue surface 114 of the rail 110, and FIG. 21 additionally shows an embodiment of the vehicle 120 that is configured to move along, as indicated with arrow 990, and be in contact with the toothed vehicle surface 114 of the rail 110.

According to one embodiment, shown in FIGS. 20 and 21, the vehicle surface 113 is toothed. In other words, the vehicle surface 113 comprises a plurality of teeth 1132 along the vehicle surface 113, and gaps 1134 between the teeth 1132. According to one embodiment, the teeth can be vertical relative to a base 1136 of the vehicle surface 113, as shown in FIG. 20. According to another embodiment, the teeth can be tilted relative to the base 1136 of the vehicle surface 113, as shown in FIG. 21.

According to one embodiment, the vehicle 120 comprises at least one toothed wheel 129 that is configured to be in contact with and roll along the toothed vehicle surface 113 of the rail 110. Thus, an orientation of wheel teeth 1292 of the toothed wheel 129 correspond to the orientation of the teeth 1132 of the vehicle surface 112 of the rail 110. For example, wheel teeth 1292 of a toothed wheel 129 are tilted similarly to the teeth 1132 of the vehicle surface 113 with which the toothed wheel 129 is configured to be in contact and move along, as shown in FIG. 21. Similarly, a toothed wheel 129 that is configured to be in contact and move along the toothed vehicle surface 113 having vertical teeth 1132, shown in FIG. 20, has vertical wheel teeth 1292 as well.

The vehicle 120 that comprises at least one toothed wheel 129 can move along the rail 110 in any mechanism, for example, by using a vehicle cable 128 as shown for example in 19, and the like. Preferably, the vehicle 120 that comprises at least one toothed wheel 129 can move along the rail 110 by using a motor 127 as shown for example in FIG. 13.

Returning now to FIG. 20. According to one embodiment, the tissue surface 114 of the rail 110 is folded. In other words, according to this embodiment, the tissue surface 114 comprises multiple folds 1142 along the length of the tissue surface 114. The folds 1142 increase the surface area of the tissue surface 114 and tighten the attachment of the tissue surface 114 of the rail 110 with the elevated tissue 520. The rail 110 shown in FIG. 21 is tightly attached to the elevated tissue 520 because of the folded tissue surface 114 of the rail 110.

Figure 22:
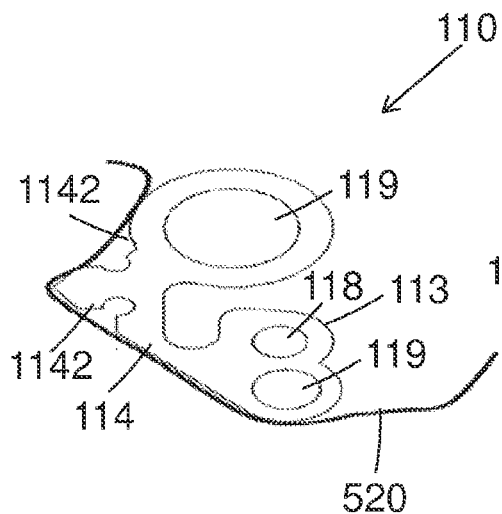
FIGS. 22 and 23 schematically illustrate, according to some exemplary embodiments, cross-sectional views of rails comprising a folded tissue surface having various structures of folds.
Figure 23:
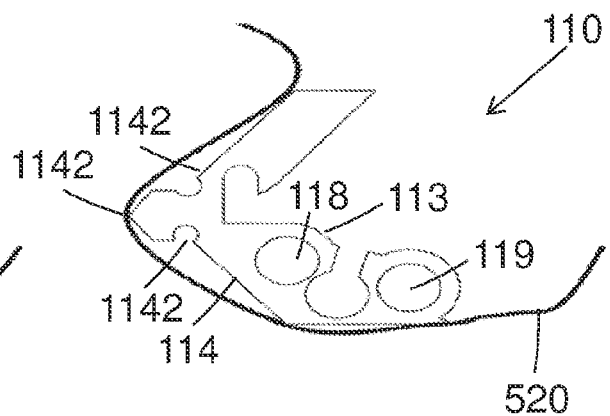

Referring now to FIGS. 22 and 23, schematically illustrating, according to some exemplary embodiments, cross-sectional views of rails comprising a folded tissue surface having various structures of folds. The folds 1142 of the folded tissue surface 114 of the rail 110 can have any type of structure and relative sizes, examples of which are shown in FIGS. 22 and 23. FIGS. 22 and 23 also show the interaction of the elevated tissue 520 with the folded tissue surface. The folds 1142 increase the surface area of tissue surface 114, thus tightening the attachment of the elevated tissue with the folded tissue surface 114 of the rail 110. This embodiment decreases the chance of separation between the rail 110 and the elevated tissue 520, or sliding of the rail 110 off the elevated tissue 520, during manipulation, for example cutting, of the elevated tissue 520.

Figure 24:
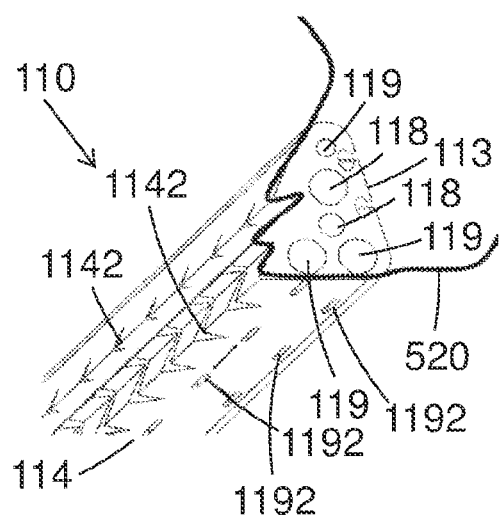
FIGS. 24 and 25 schematically illustrate, according to an exemplary embodiment, perspective views of rails comprising a folded tissue surface having various structures of folds.
Figure 25:
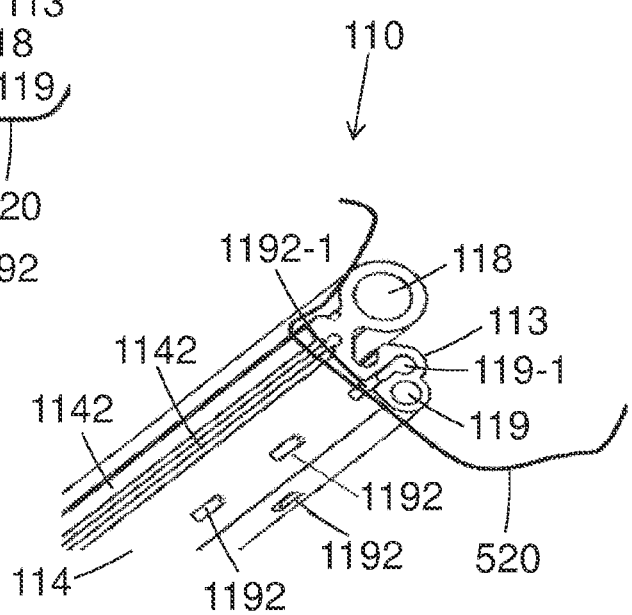

Referring now to FIGS. 24 and 25, schematically illustrating, according to an exemplary embodiment, perspective views of rails comprising a folded tissue surface having various structures of folds. FIGS. 24 and 25 show a three dimensional structure of two exemplary folded tissue surface 114 of a rail 110, and how the folds 1142 increase the surface area of the tissue surface 114.

FIGS. 22-25 show another embodiment of the rail 110, according to which the rail 110 comprises at least one hardening pipe 118 passing internally inside the rail 110. The hardening pipe 118 passes until a control panel 80 and is configured to allow passage of fluid through the hardening pipe 118 in order to harden and make the rail 110 more rigid, for example after the rail 110 has surrounded an elevated tissue 520, for purposes described above in relation to the inflatable elements 111. Any type of fluid is under the scope of the present subject matter, for example a gas like air, nitrogen, carbon dioxide, and the like; or a liquid like water, saline, oil, and the like.

FIGS. 22-25 show a further embodiment of the rail 110, according to which the rail 110 comprises at least one suction pipe 119 passing internally inside the rail 110, and at least one suction orifice 1192 on the tissue surface 114 that is fluidically connected to the suction pipe 119. In FIG. 25 a cross-section of the rail 110 passes through a specific suction pipe 119-1 and a specific suction orifice 1192-1 fluidically connected to the specific suction pipe 119, in order to illustrate the fluid connection between the suction pipe 119 and the suction orifice 1192. The suction pipe 119 passes until a control panel 80. The suction pipe 119 is configured to allow formation of negative gas pressure at the suction orifice 1192 in order to suck the elevated tissue 520 that is in contact with the tissue surface 114 and the at least one suction orifice 1192 on the tissue surface 114. The suction of the elevated tissue 520 through the at least one suction orifice 1192 tightens the contact of the rail 110 with the elevated tissue 520.

Figure 26:
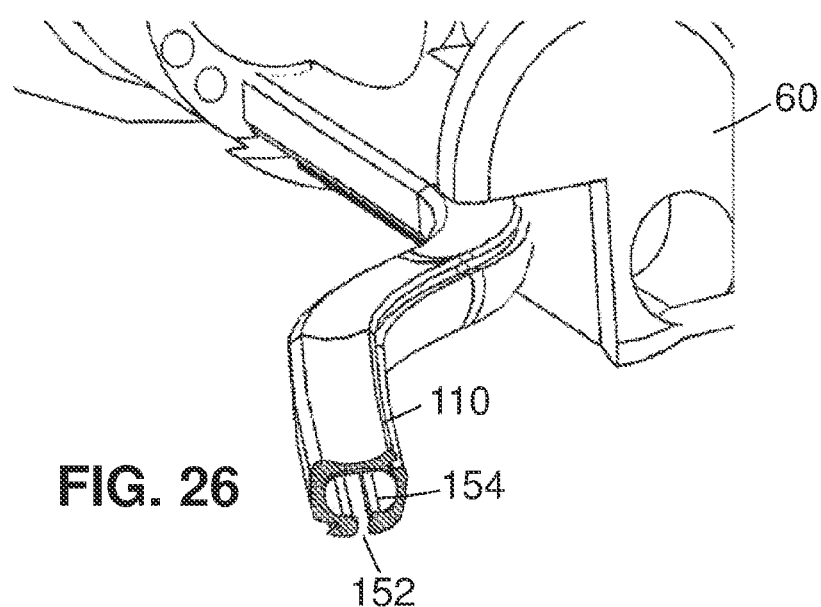
FIG. 26 schematically illustrates, according to an exemplary embodiment, a rail having a tube-like structure and a longitudinal slot along the rail.

Referring now to FIG. 26, schematically illustrating, according to an exemplary embodiment, a rail having a tube-like structure and a longitudinal slot along the rail. FIG. 26 shows a multi-lumen 70 from which a rail 110 extends. The rail 110 is cross-sectioned in order to show the structure of a profile of the rail 110. According to the embodiment shown in FIG. 26, the rail 110 has a tube like structure, and a longitudinal slot 152 along the rail 110. Due to the tube-like structure of the rail 110, the rail also comprises an internal space 154.

Figure 27:
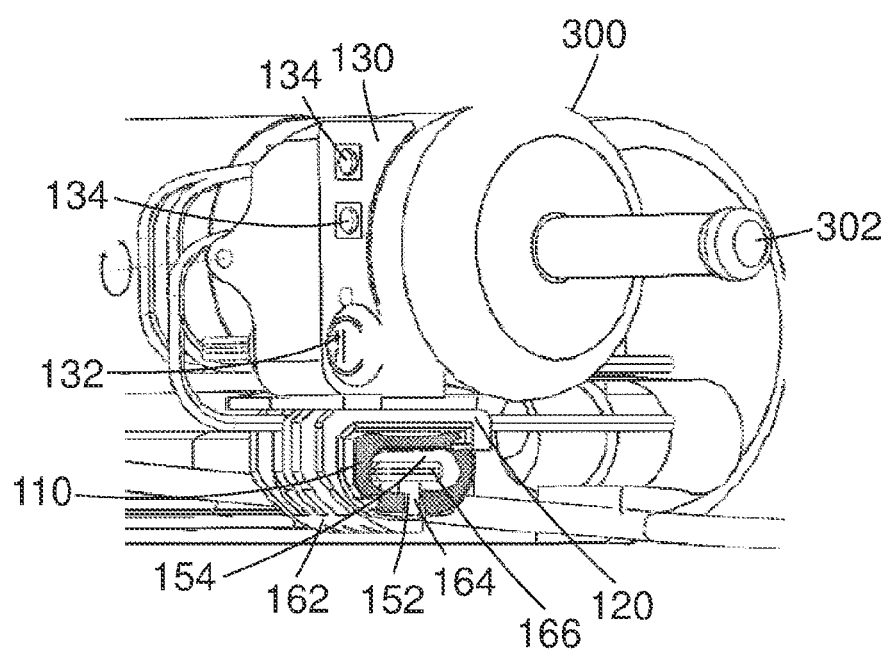
FIG. 27 schematically illustrates, according to an exemplary embodiment, a vehicle comprising at least one vehicle bearing configured to be accommodated in a rail having a tube-like structure and a longitudinal slot along the rail.

Referring now to FIG. 27, schematically illustrating, according to an exemplary embodiment, a vehicle comprising at least one vehicle bearing configured to be accommodated in a rail having a tube-like structure and a longitudinal slot along the rail. FIG. 27 shows a vehicle 120, a cutting tool 300, comprising a blade 302, attached to the vehicle 120, and an imaging device 130, comprising an imaging device lens 132 and at least one, for example two, light sources 134, the imaging device 130 also attached to the vehicle 130. The vehicle 120 in FIG. 27 is configured to attach to and move along a rail 110 having a tube-like structure and a longitudinal slot 152 along the rail 110, described in detail in FIG. 26. For this purpose, the vehicle comprises a bearing base 162 attached to a lower side of the vehicle 120, at least one bearing axis 164 attached to an edge of the bearing base 162, and a vehicle bearing 166 attached to each bearing base 16. The vehicle bearing 166 is configured to be accommodated in the internal space 154 of the rail 110, and the bearing axis 164 is configured to pass through longitudinal slot 152 of the rail 110, thus connecting the vehicle bearing 166 that is inside the internal space 154 of the rail 110, with the bearing base 162 that is out of the rail 110. During movement of the vehicle 120 along the rail 110, the at least one vehicle bearing 166 facilitates attachment of the vehicle 120 to the rail 110, and reduces friction forces with the rail 110 in order to allow smooth movement of the vehicle 120 along the rail 110. As can be seen in FIG. 27, the vehicle bearings 166 are attached to a bottom side of the vehicle 120, and the vehicle 120 is positioned above the rail 110. However, this relative position of the vehicle 120 above the rail 110 is only exemplary, and should not be considered as limiting the scope of the present subject matter. The vehicle 120 can be positioned in any position relative to rail 110, for example above the rail 110, as described above, aside the rail 110, or below the rail 110, as described hereinafter, and the like.

Figure 28:
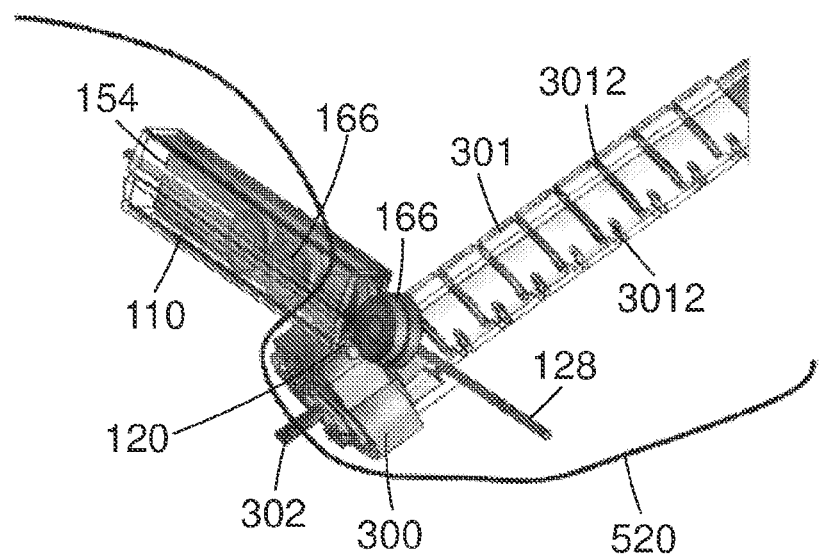
FIG. 28 schematically illustrates, according to an exemplary embodiment, a vehicle comprising at least one vehicle bearing configured to be positioned below a rail.

Referring now to FIG. 28, schematically illustrating, according to an exemplary embodiment, a vehicle comprising at least one vehicle bearing configured to be positioned below a rail. FIG. 28 illustrates a vehicle 120 comprising at least one vehicle bearing 166, for example four vehicle bearings 166, as seen in FIG. 28. The at least one vehicle bearing 166 is configured to be accommodated in an internal space 154 of the rail 110. Three of the four vehicle bearings 166 are seen inside the rail 110 in FIG. 28. The vehicle is moved along the rail by using a vehicle cable 128 attached to the vehicle 120, as described above. As can be further seen in FIG. 28, the vehicle 120 is positioned under the rail 110.

Additional embodiments of the cutting tool 300 that is attached to the vehicle 120 are shown in FIG. 28. The blade 302 of the cutting tool 300 is shown. The cable 301 that is attached to the cutting tool 300 is slotted, namely comprising multiple cable slots 3012, preferably vertically to the length of the cable 301. Some of the cable slots 3012 can be longer than other cable slots 3012. The cable slots 3012 confer flexibility to the cable 301, which is important for smooth movement and passage of the cable 301 through the endoscope 60, and occasionally through the multi-lumen 70.

Figure 29:
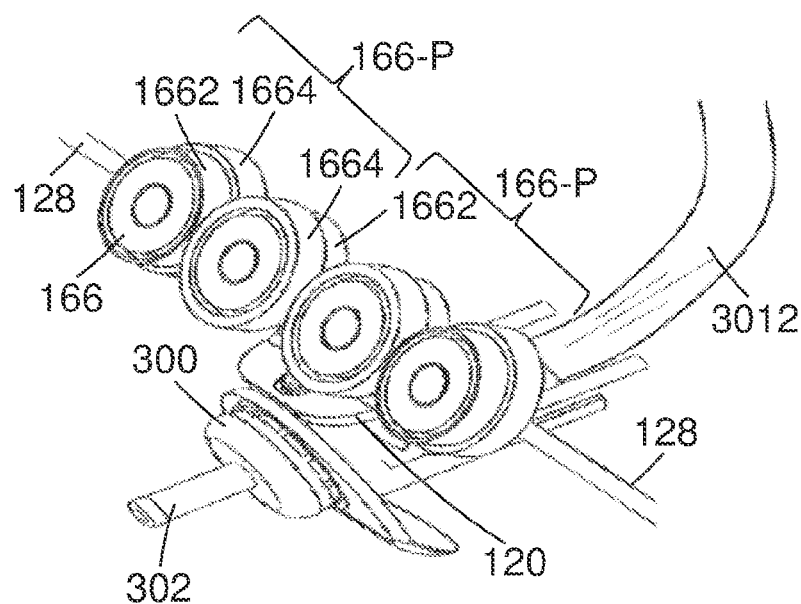
FIG. 29 schematically illustrates, according to an exemplary embodiment, integrated vehicle bearings of a vehicle.

Referring now to FIG. 29, schematically illustrating, according to an exemplary embodiment, integrated vehicle bearings of a vehicle. FIG. 29 shows a vehicle 120 similar to the vehicle 120 shown in FIG. 28. A cutting tool 300, with a blade 302 and a cable 301, is attached to the vehicle 120. In this embodiment, a vehicle cable 128 is attached to one side of the vehicle 120, and another vehicle cable 128 is attached to another side of the vehicle 120. Further seen in FIG. 29 is that the four vehicle bearings 166 of the vehicle 120 are divided to two pairs 116-P of integrated vehicle bearings 166. The integration of each two vehicle bearings 166 can be achieved, for example, by a graduated structure of a circumference of the vehicle bearings 166. The circumference of the vehicle bearing 166 comprises a lower stair 1662 and an upper stair 1664. In the pair 116-P of the integrate vehicle bearings 166, a lower stair 1662 of one vehicle bearing 166 is positioned aside an upper stair 1664 of the second vehicle bearing 166, and vice versa. This enables integration of the vehicle bearings 166 each in pair 166-P. An advantage of the integrated vehicle bearings 166 is that this feature stabilizes the movement of the vehicle 120 along the rail 110, and renders the movement more smooth, because the contact of the two vehicle bearings 166 in each pair 166-P prevents unnecessary friction of the vehicle bearings 166 that can be present in the path of the vehicle 120.

Figure 30:
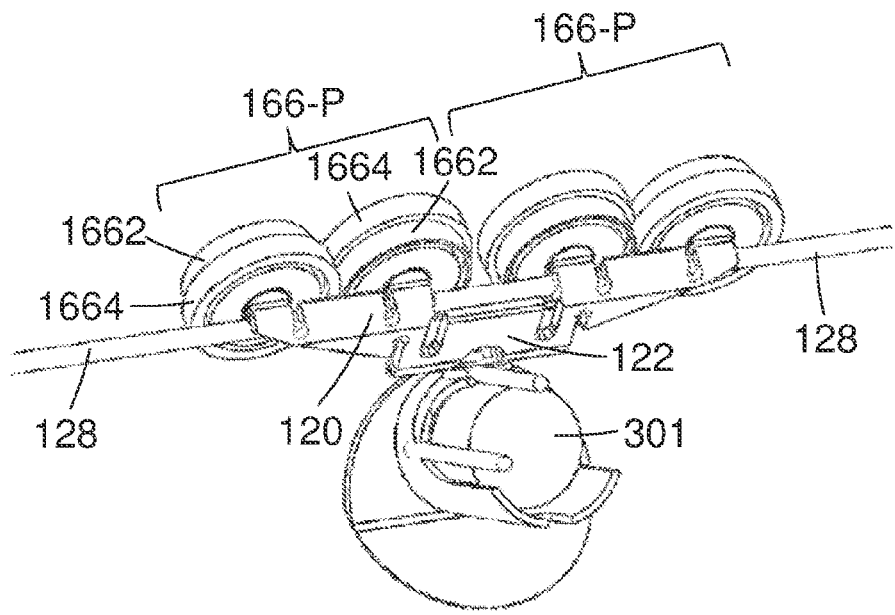
FIG. 30 schematically illustrates, according to an exemplary embodiment, another perspective view of integrated vehicle bearings of a vehicle.

Referring now to FIG. 30, schematically illustrating, according to an exemplary embodiment, another perspective view of integrated vehicle bearings of a vehicle. FIG. 30 show another perspective view of the vehicle 120 shown in FIG. 29. The cutting tool 300 is attached to the bottom of the vehicle 120, and the cable 301 of the cutting tool 300 is seen cross-sectioned in FIG. 30. The two pairs 116-6 of integrated vehicle bearings 116 and the mechanism of integration of the vehicle bearings 116, as described in FIG. 29 are clearly seen. A clear view of an exemplary embodiment of the vehicle 120 is shown in FIG. 30. According to this embodiment, the vehicle 120 is elongated, and the vehicle bearings 166 are connected to the vehicle 120. In addition, a connector 122 is attached to the vehicle 120, in this embodiment, to a bottom side of the vehicle 120. The cutting tool 300 is connected to the connector 122, thereby the cutting tool 300 is connected to the vehicle 120.

Figure 31:
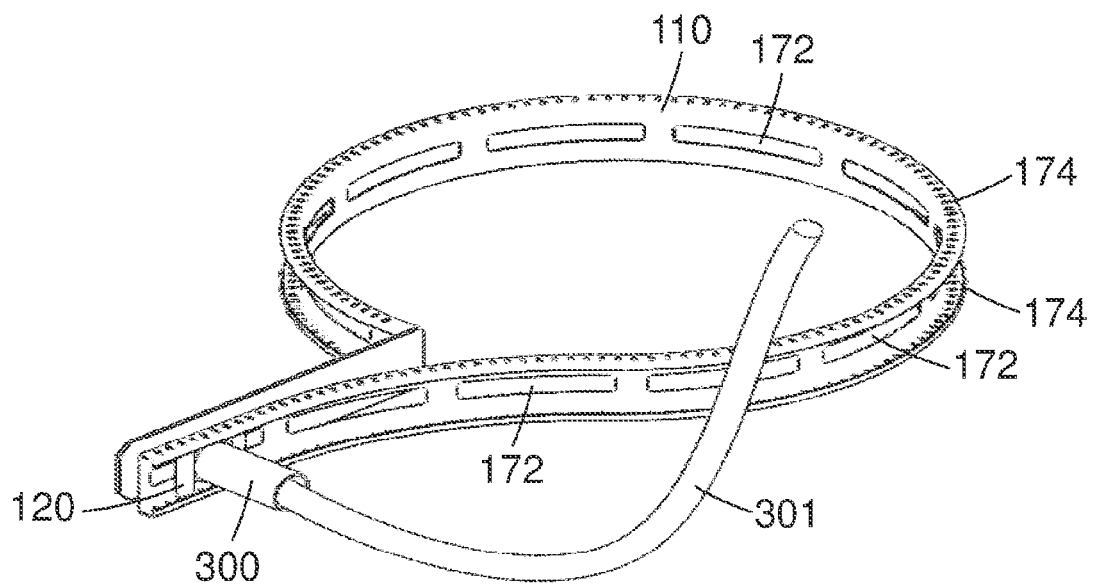
FIG. 31 schematically illustrates, according to an exemplary embodiment, a rail comprising multiple elongated windows, a vehicle and a cutting tool configured to operate with the rail comprising multiple elongated windows.

Referring now to FIG. 31, schematically illustrating, according to an exemplary embodiment, a rail comprising multiple elongated windows, a vehicle and a cutting tool configured to operate with the rail comprising multiple elongated windows. FIG. 31 shows an embodiment of a rail 110 that has a strip-like structure with multiple elongated windows 172 along the rail 110. In addition, the rail 110 comprises extended rims 174 along the two sides of the strip-like structure. The rims 174 are configured to trap the vehicle 120 in between them, and the vehicle 120 is configured to be trapped by the rims 174 close to the strip-like structure of the rail 110, and move along the rail 110. FIG. 31 further shows a cutting tool 300 attached to the vehicle 120, and a cable 301 extending from the cutting tool 300.

Figure 32:
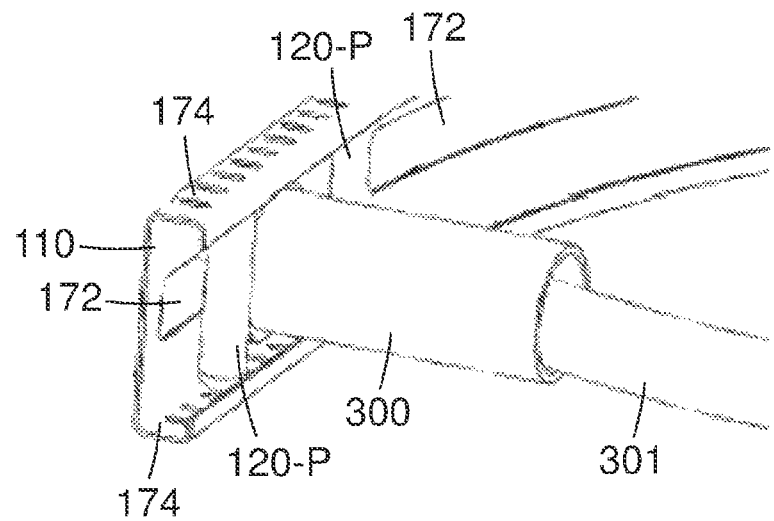
FIGS. 32 and 33 schematically illustrate, according to an exemplary embodiment, different projections of a close-up view of a rail comprising multiple elongated windows, a vehicle and a cutting tool configured to operate with the rail comprising multiple elongated windows.
Figure 33:
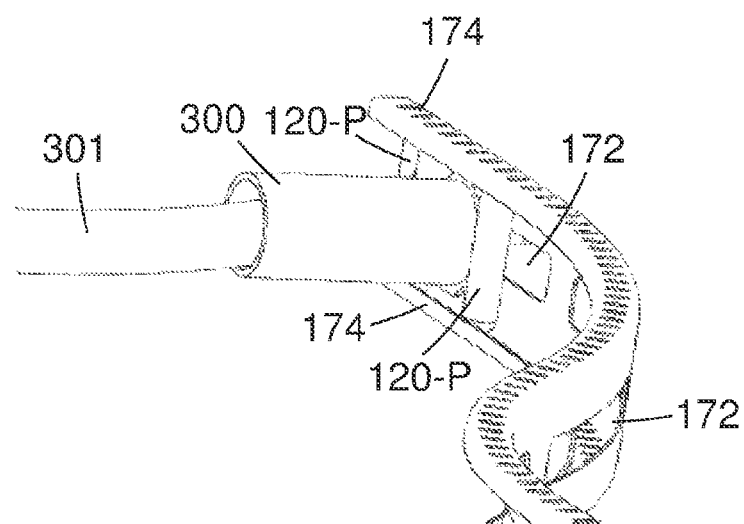

Referring now to FIGS. 32 and 33, schematically illustrating, according to an exemplary embodiment, different projections of a close-up view of a rail comprising multiple elongated windows, a vehicle and a cutting tool configured to operate with the rail comprising multiple elongated windows. FIGS. 32 and 33 clearly show the vehicle 120 trapped by the rims 174 of the strip-like structure of the rail 110, and the cutting device 300 attached to the vehicle 120. In this embodiment, the vehicle 120 comprises two vehicle parts 120-P that are configured to be trapped between the rims 174 of the rail 110. The parts 120-P of the vehicle 120 can have any structure that is suitable to be trapped by the rims 174 of the rail 110, for example a rod-like structure, as seen in FIGS. 32 and 33. The two parts 120-P of the vehicle are connected to both sides of the cutting tool 300. Thus, the cutting tool 300 moves together with the two parts 120-P of the vehicle 120 along the rail 110.

Figure 34:
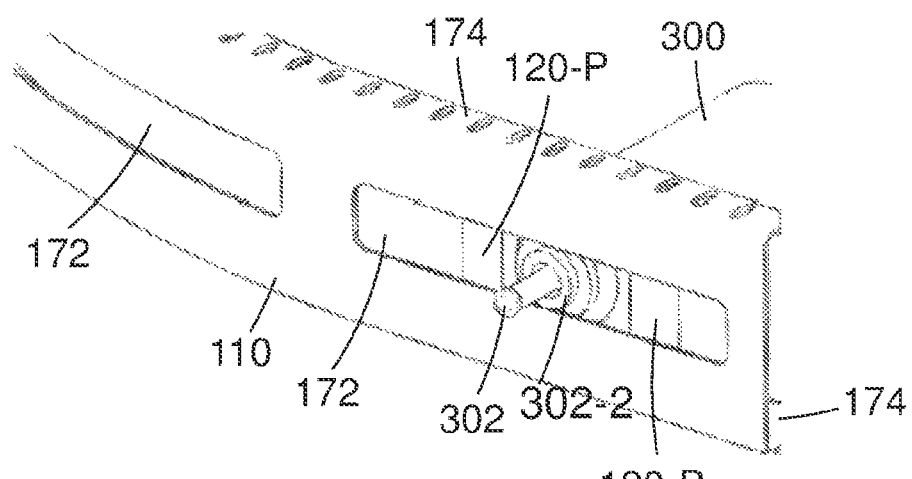
FIG. 34 schematically illustrates, according to an exemplary embodiment, a rail comprising multiple elongated windows, and a blade, a cutting probe, or an electrode of a cutting tool extending through a window.

Referring now to FIG. 34, schematically illustrating, according to an exemplary embodiment, a rail comprising multiple elongated windows, and a blade, a cutting probe, or an electrode of a cutting tool extending through a window. The cutting tool will be referred to as a blade. FIG. 34 shows the rail 110 comprising multiple elongated windows 172 illustrated in FIGS. 31-33, from a side of the elevated tissue. The windows height should be smaller than the height of the rail. When there is a desire to cut the elevated tissue, the blade 302 is extended out of the cutting tool 300 through the window 172, and cuts the elevated tissue during movement of the vehicle 120. The blade is protected within an isolation ring 302-2. When the blade 302 reaches an edge of the window 172, the blade 302 is returned back into the cutting tool 300, the vehicle 120 moves further until the blade 302 is positioned in front of a next window, and the blade 302 is extended out again from the cutting tool 300 and through the window 172 in order to cut the elevated tissue. As a result of this procedure, the cutting of the elevated tissue is broken, or fragmented. In order to complete the cutting, the rail 110 can be moved a little and brought to a position where the un-cut areas are in front of windows, and the cutting procedure described above is performed again in order to cut the un-cut areas. Another solution for this non-continuous cutting of the elevated tissue due to the presence of windows 172 in the rail 110 is described hereinafter.

Figure 35:
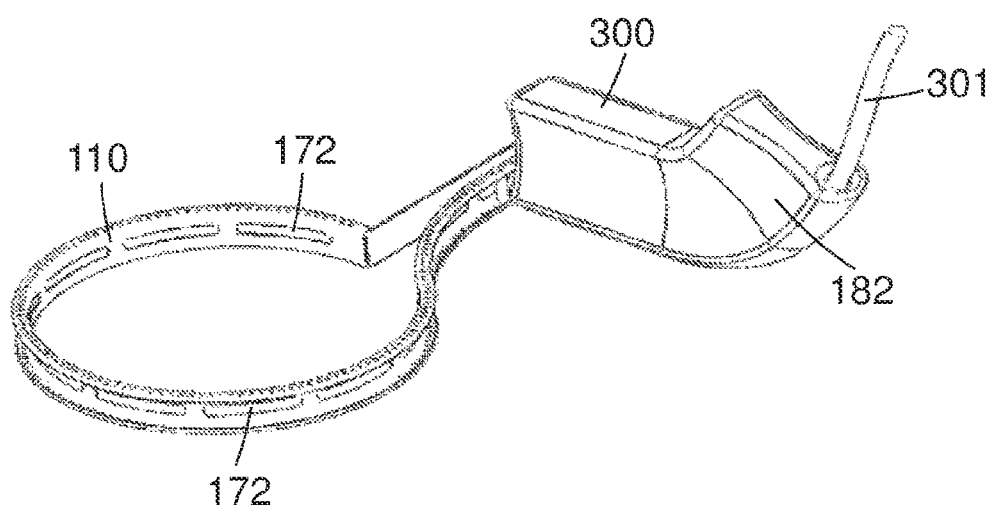
FIG. 35 schematically illustrates, according to an exemplary embodiment, a vehicle with a cutting tool that are configured to be held and moved manually.

Referring now to FIG. 35, schematically illustrating, according to an exemplary embodiment, a vehicle with a cutting tool that are configured to be held and moved manually. FIG. 35 is similar to FIG. 31, except that a handle 182 is attached to the cutting tool 300. The handle 182 is configured to be held by fingers of an operator, thus allowing the operator to manually move the cutting tool 300 with the vehicle 120 along the rail 120. It should be noted that this embodiment of a handle 182 attached to the cutting tool 300 should be considered as limiting the scope of the present subject matter. The handle 182 can be attached directly to any type of vehicle 120 that is configured to move along any type of rail 110, or to any type of tool that is attached to the vehicle 120. This embodiment of a handle 182 attached to the vehicle 120, or to the tool that is attached to the vehicle 120, is suitable, for example, to open surgeries where the elevated tissue that is to be manipulated, for example removed, with the system 1 of the present subject matter, can be accessed by hands of an operator of the system 1.

Figure 36:
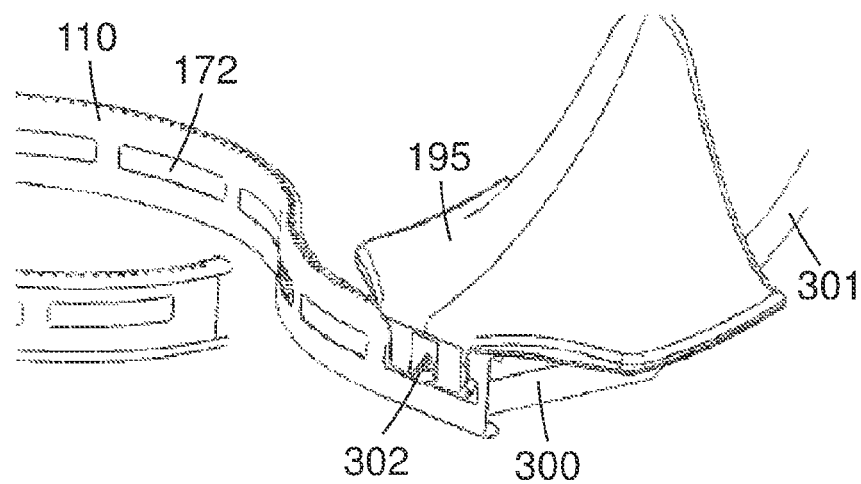
FIG. 36 schematically illustrates, according to an exemplary embodiment, a tissue remover attached to cutting tool.

Referring now to FIG. 36, schematically illustrating, according to an exemplary embodiment, a tissue remover attached to cutting tool. FIG. 36 is similar to FIG. 34 except that view is further away from the rail 110. During the cutting of the elevated tissue, particularly when the cutting is in an advanced stage inside the elevated tissue, part of the elevated tissue can cover the rail 110, the vehicle 120 and the cutting tool 300, thereby interfering with the movement of the vehicle 120 along the rail 110, and the cutting process. In order to prevent such an interference, a tissue remover 195 is attached to an upper part of the cutting tool 300. Alternatively, the tissue remover 195 can be attached to an upper part of the vehicle 120. The tissue remover 195 has a substantially flat structure, and can be attached substantially diagonally above the cutting tool 300, or the vehicle 120. Thus, the elevated tissue 520 is removed away from the cutting tool 300, or the vehicle 120.

Figure 37:
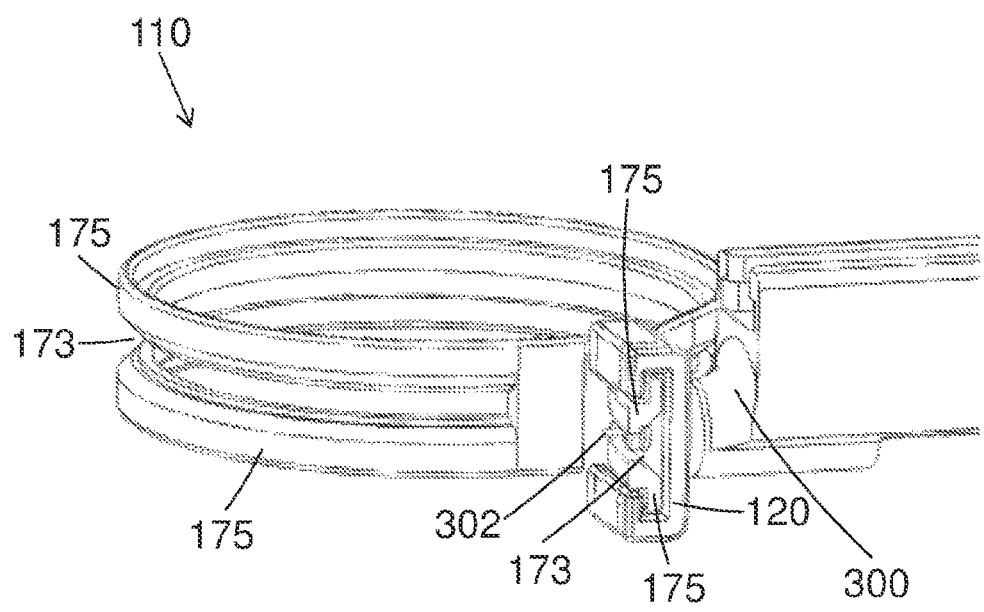
FIGS. 37 and 38 schematically illustrate, according to an exemplary embodiment, different views of a rail comprising a continuous window, a vehicle and a cutting tool configured to operate with the rail comprising a continuous window.
Figure 38:
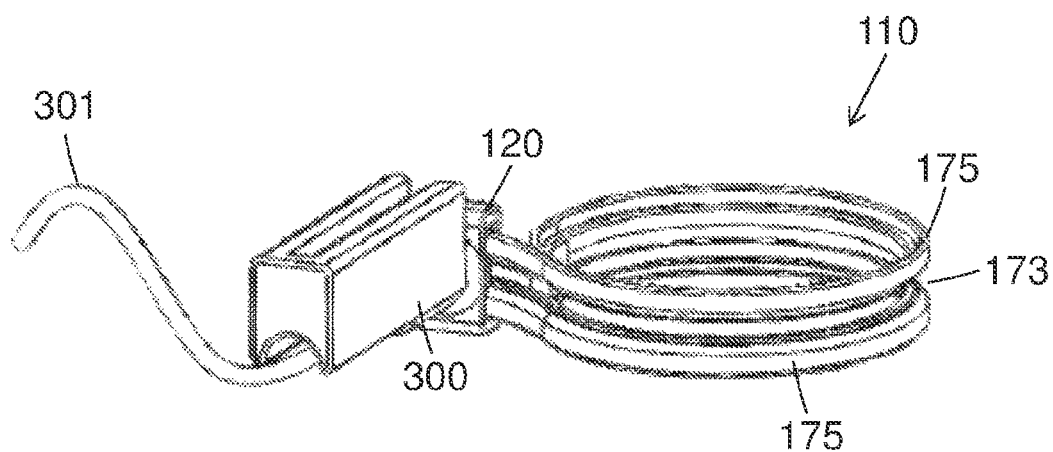

Referring now to FIGS. 37 and 38, schematically illustrating, according to an exemplary embodiment, different views of a rail comprising a continuous window, a vehicle and a cutting tool configured to operate with the rail comprising a continuous window. The rail 110 illustrated in FIGS. 37-38 solves the problem of non-continuous cutting of the elevated tissue caused by the rail 110 comprising multiple elongated windows 172 described above. The rail 110 shown in FIG. 37-38 is similar to the aforementioned rail 110 comprising multiple elongated windows 172, except that instead of comprising multiple elongated windows 172, the rail 110 comprises a continuous window 173. This enables continuous cutting of the elevated tissue with the blade 302 that extends through the continuous window 172, as can be seen in FIG. 37.

As a result of the continuous window 173, the strip-like structure of the 110 is divided to two strips 175, when the gap between the two strips 175 is the continuous window 173. FIG. 37 also illustrates a vehicle 120 that is configured to attach and move along the rail 110 that comprises two strips 175. In this embodiment, the vehicle 120 is configured to enclose from the outside the two strips 1f, while allowing to the blade 302 of the cutting tool 300 that is attached to the vehicle 120 to extend through the continuous window 173 that is between the two strips 175.

Figure 39:
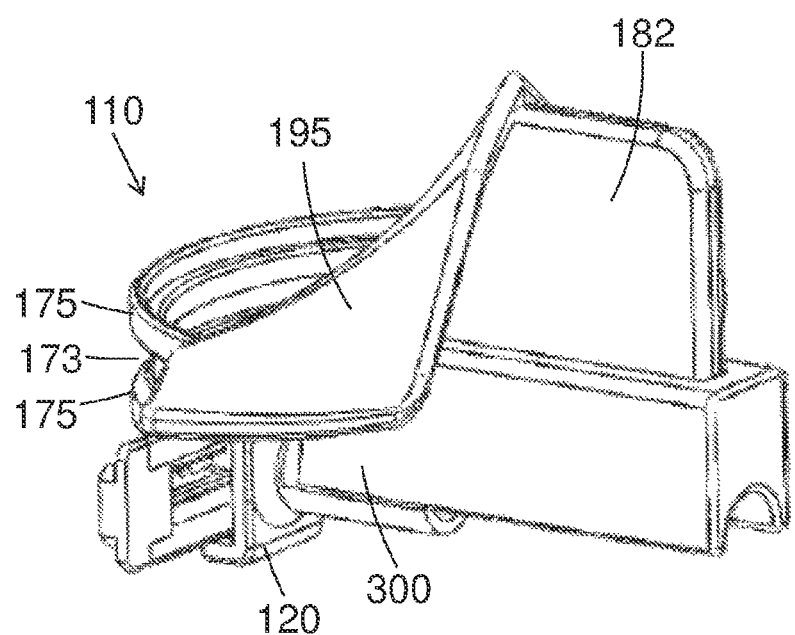
FIG. 39 schematically illustrates, according to an exemplary embodiment, a rail comprising two strips and a continuous window, a vehicle configured to attached and move along the rail, and a cutting tool, and a handle and a tissue remover attached to the cutting tool.

Referring now to FIG. 39, schematically illustrating, according to an exemplary embodiment, a rail comprising two strips and a continuous window, a vehicle configured to attached and move along the rail, and a cutting tool, and a handle and a tissue remover attached to the cutting tool. The rail 110, the vehicle 120 and the cutting tool 300 illustrated in FIG. 39 are similar to the rail 110, the vehicle 120 and the cutting tool 300 that are shown in FIGS. 37-38. The embodiments of the handle 182 shown in FIG. 39 are similar to the embodiments of the handle 182 shown in FIG. 35, and the embodiments of the tissue remover 195 shown in FIG. 39 are similar to the embodiments of the tissue remover 195 shown in FIG. 36.

Figure 40:
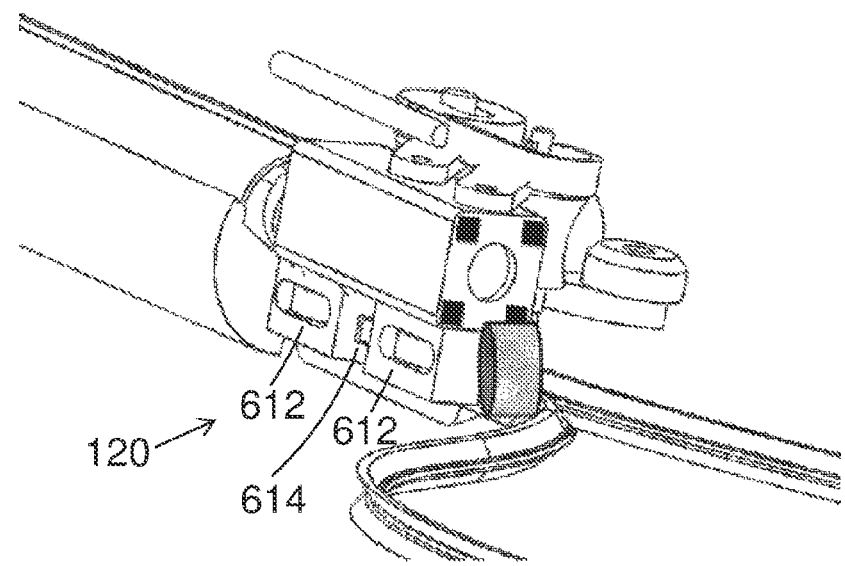
FIG. 40 schematically illustrates, according to an exemplary embodiment, an articulated vehicle.

Referring now to FIG. 40, schematically illustrating, according to an exemplary embodiment, an articulated vehicle. The vehicle 120 shown in FIG. 40 has the same embodiments as the vehicle 120 shown in FIG. 12. An additional embodiment is shown here, according to which the vehicle is articulated. Thus, the vehicle 120 comprises multiple sections 612 linked by pivoting joints 614. For example, the vehicle 120 shown in FIG. 40 comprises two sections 612 linked by a pivoting joint 614. This embodiment confers flexibility to the vehicle 120, and improved ability for the vehicle 120 to turn, particularly in sharp curves, of the rail 110.

Figure 41:
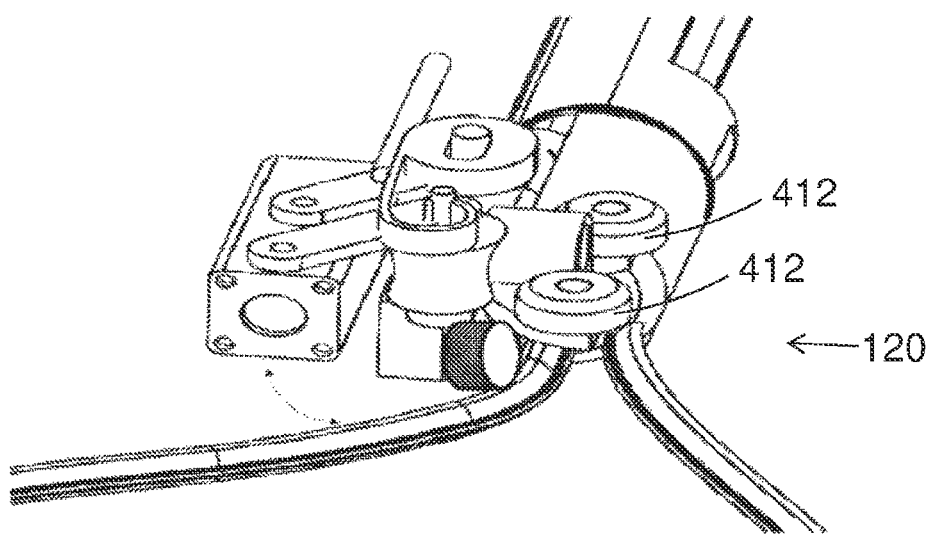
FIG. 41 schematically illustrates, according to an exemplary embodiment, a vehicle comprising sliding wheels.

Referring now to FIG. 41, schematically illustrating, according to an exemplary embodiment, a vehicle comprising sliding wheels. The vehicle shown in FIG. 41 has the same embodiments as the vehicle 120 shown in FIG. 14. An additional embodiment is shown here, according to which the vehicle 120 comprises at least one sliding wheel 412. For example, the vehicle 120 shown in FIG. 41 comprises two sliding wheels 412. The at least one sliding wheel 412 is attached to a side of the vehicle 120 that faces the elevated tissue, and is configured to slide over the elevated tissue.

Figure 42A:
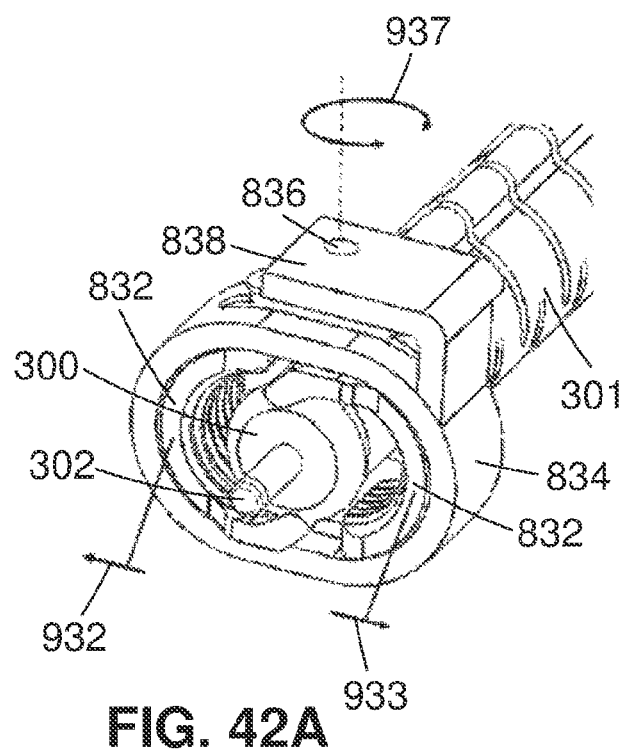
FIGS. 42A-B schematically illustrate, according to exemplary embodiments, a holder of tool in a form of a clamp.
Figure 42B:
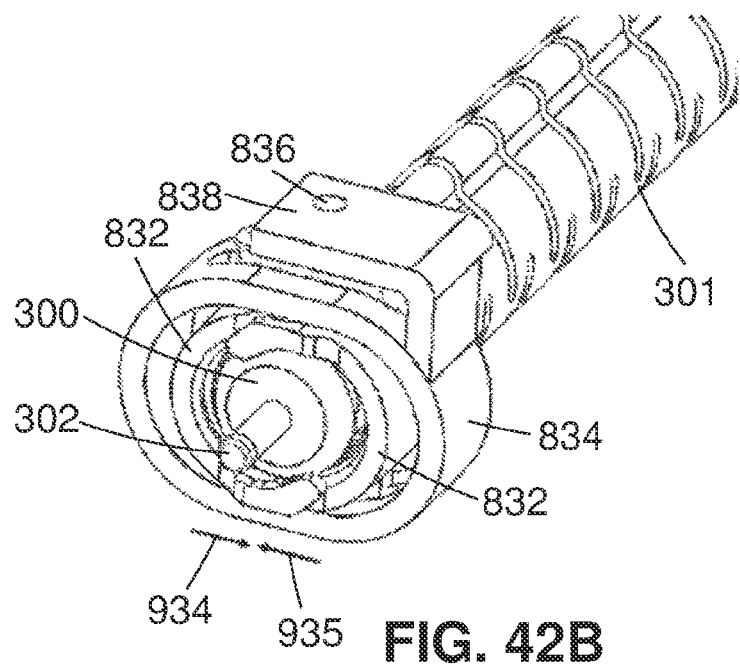

Referring now to FIGS. 42A-B, schematically illustrating, according to an exemplary embodiment, a holder of tool in a form of a clamp. FIGS. 42A-B illustrate an open state and a closed state, respectively, of a holder of a tool in a form of a clamp. The holder comprises two clamp arms 832 that are configured to be in an open state, as shown in FIG. 42A, and in a closed state, as shown in FIG. 42B. When the clamp arms 832 are in the open state, shown with arrows 932 and 933, a tool, for example a cutting tool 300, can be inserted between the clamp arms 832, or removed from the clamp arms 832. When the clamp arms 832 are in the closed state, shown with arrows 934 and 935, the clamp arms 832 hold the tool. According to one embodiment, the clamp arms 832 can be housed in a clamp housing 834, for example in order to protect the clamp arms 832. The clamp arms 832, or the clamp housing 834, are pivotally connected, with a clamp pivot 836, to a clamp holder 838, and the clamp holder is attached to the vehicle. The clamp pivot 836 allows swiveling of the clamp arms 832, or the clamp housing 834, about the clamp pivot 836, in directions indicated with arrow 937, thus allowing the tool, for example the cutting tool 300, and the blade 302 of the cutting tool 300, to swivel to the left and right in relation to the clamp pivot 836. This embodiment allows, in one hand, holding the tool, for example the cutting tool 300, by the vehicle, and on the other hand, this embodiment allows an increased degree of freedom of movement of the tool.

Figure 43:
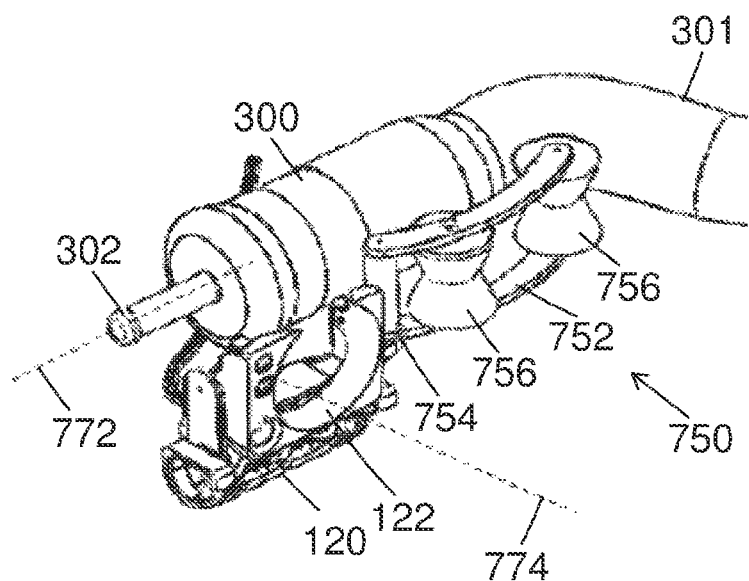
FIGS. 43-44 schematically illustrate, according to an exemplary embodiment, a lock of a tool.
Figure 44:
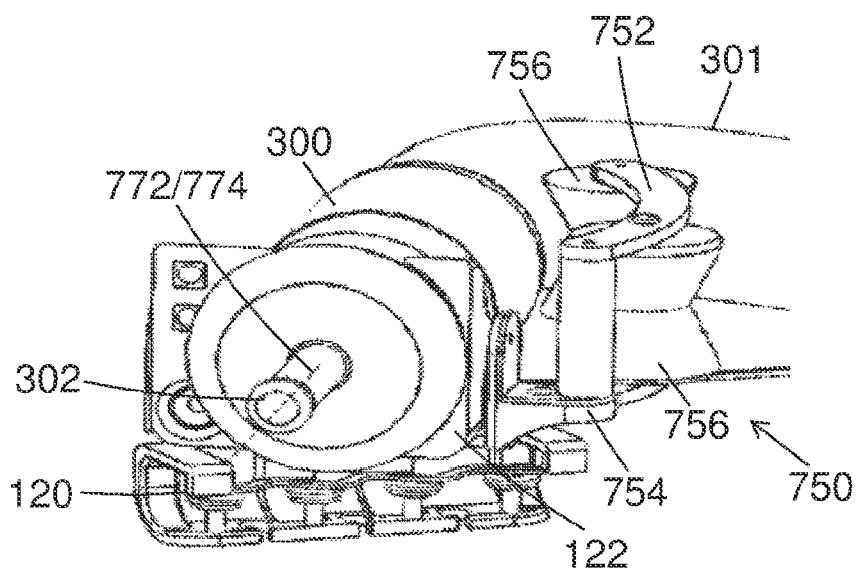

Referring now to FIGS. 43-44, schematically illustrating, according to an exemplary embodiment, a lock of a tool. FIGS. 43-44 show a lock 750 for locking a tool, for example a cutting tool 300, to a connector 122 of a vehicle 120. According to a state of the lock 750, the tool can be either free, as shown in FIG. 43, or locked in the connector 122, as shown in FIG. 44. FIG. 43 shows a vehicle 120 comprising a connector 122 configured to connect a tool to the vehicle 120. Aside the vehicle 120 there is a cutting tool 300 comprising a cable 301 and a blade 302. Broken line 772 indicates a blade line 772 that runs along the blade 302. Broken line 774 indicates a locked blade line 774 that runs along the blade 302 when the cutting tool 300 is locked to the connector 122. In FIG. 43, which shows the cutting tool 300 in a free state, the blade line 772 is substantially vertical to the locked blade line 774. In order to lock the cutting tool 300 in the connector 122, the cutting tool 300 has to swivel until the blade line 772 overlaps with the locked blade line 774, is shown in FIG. 44. This is achieved with the lock 750.

The lock 750 comprises a lock frame 752 pivotally connected, with a lock pivot 754, to a side of the connector 122. At least one, for example two, lock presses 756 are framed by the lock frame 752. The lock press 756 can have a cylindrical shape, or preferably a curved cylindrical shape having a concavity, as shown in FIGS. 43-44. The lock press 756 can turn around its longitudinal axis. In the free state, shown in FIG. 43, the lock frame 752 is in a first position that allows the cutting tool 300 and the cable 301 of the cutting tool 300, to rest aside the connector 122, when the blade line 772 is substantially vertical to the locked blade line 774. In order to lock the cutting tool 300 in the connector 122, the lock frame 752 is configured to turn about the lock pivot 754 in a direction of the cutting tool 300 and the cable 301, until the lock frame 752 reaches a second state, shown in FIG. 44. This causes the cutting tool 300 to turn toward the holder 122 and get locked in the holder 122, when the blade line 772 overlaps with the locked blade line 774.

Figure 45:
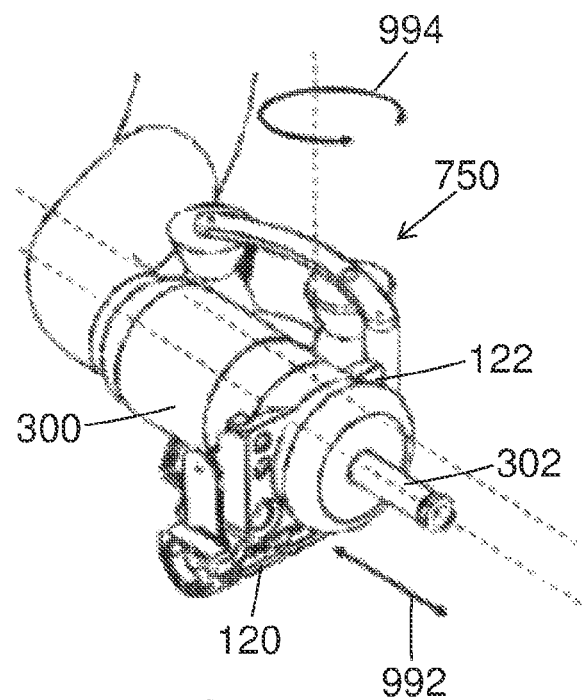
FIGS. 45-46 schematically illustrate, according to exemplary embodiments, capabilities of movement of a tool relative to a vehicle.
Figure 46:
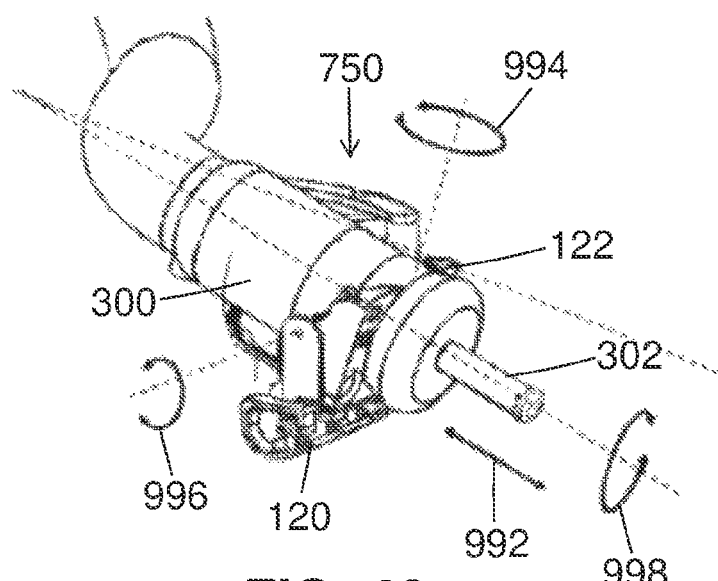
Figure 47:
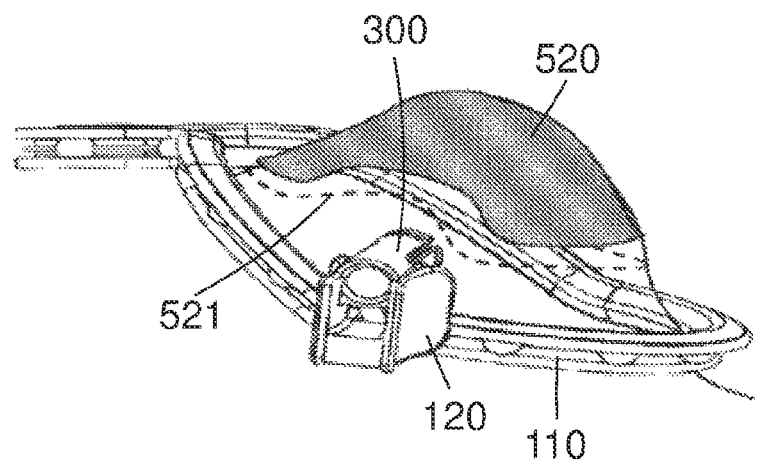
FIG. 47 schematically illustrates, according to an exemplary embodiment, a rail surrounding an elevated tissue, a vehicle moving along the rail, and a cutting tool attached to the vehicle, and cutting the elevated tissue in various directions.

Referring now to FIGS. 45-46, schematically illustrating, according to an exemplary embodiment, capabilities of movement of a tool relative to a vehicle. FIGS. 45-46 show a cutting tool 300 locked in a connector 112, similarly to the embodiments shown in FIG. 44. In order to improve cutting of the elevated tissue with the cutting tool 300, the cutting tool 300 and the connector 122 have several degrees of freedom of movement, giving the blade 302 increased maneuvering capabilities for cutting the elevated tissue. According to one embodiment, the blade 302 is configured to move in and out from the cutting tool 300, as indicated with arrow 992 in FIGS. 45 and 46. According to another embodiment, the connector 122, and as a result also the cutting tool 300 locked in the connector 122, is configured to turn left and right, as indicated with arrow 994 in FIGS. 45 and 46. According to yet another embodiment, the connector 122, and as a result also the cutting tool 300 locked in the connector 122, is configured to turn upward and downward, a indicated with arrow 996 in FIG. 46. According to still another embodiment, the blade 302 is configured to turn about its length, as indicated with arrow 998 in FIG. 46. All these embodiments allow movement of the blade 302 essentially in any desired direction and toward any desired location on the elevated tissue Referring now to FIG. 47, schematically illustrating, according to an exemplary embodiment, a rail surrounding an elevated tissue, a vehicle moving along the rail, and a cutting tool attached to the vehicle, and cutting the elevated tissue in various directions. FIG. 47 shows an example of cutting capabilities of a cutting tool 300 that has freedom to move and turn according to embodiments shown in FIGS. 45-46. The cutting line 521 in front of the cutting tool 300 is curved upwards and then downwards. This can be achieved due to the turning capabilities of the connector 122, and the cutting tool 300 locked in the connector 122, that are shown in FIGS. 45-46.

Figure 48:
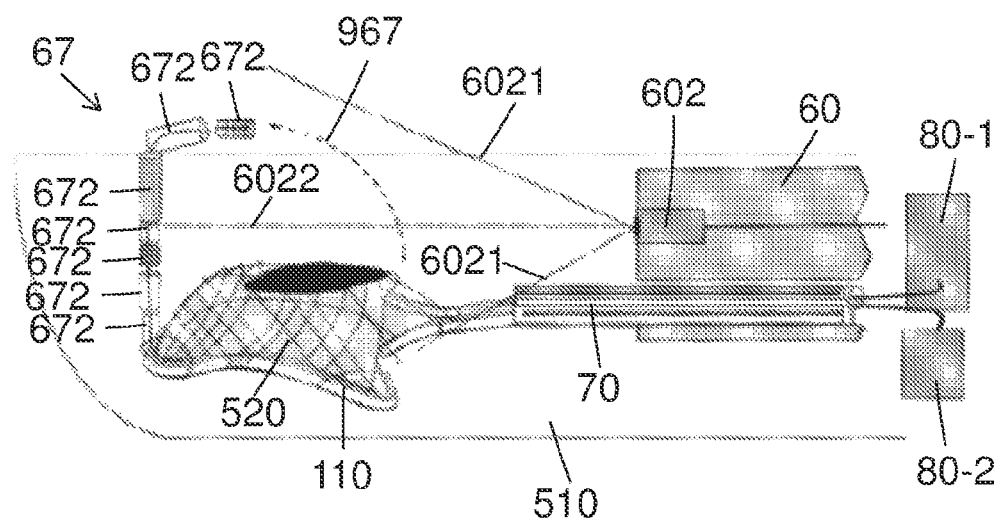
FIG. 48 schematically illustrates, according to an exemplary embodiment, a marker in a form of a collapsible marker rod attached to a rail.

Referring now to FIG. 48, schematically illustrating, according to an exemplary embodiment, a marker in a form of a collapsible marker rod attached to a rail. FIG. 48 illustrates another component of the system 1—a marker 67 configured to allow an operator to determine whether a hidden part of the rail 110 is positioned in a right place at a hidden side of the elevated tissue. As shown in FIG. 48, the endoscope 60 is placed at a right side of the elevated tissue 520. An operator of the endoscope 60 observes the elevated tissue 520 and the area of the elevated tissue 520 with an endoscope camera 602 that has a limited camera field of view 6021, designated with dashed lines 6021. An opposite side of the elevated tissue 520, relative to the endoscope 60 is hidden by the elevated tissue 520, and therefore an operator cannot see the opposite side of the elevated tissue 520. Therefore, the operator cannot see whether the rail 110 that is deployed around the elevated tissue 520 is placed in a desired position at the hidden side of the elevated tissue 520. The marker 67 is designed to provide a solution for this problem.

According to one embodiment, the marker 67 is a collapsible marker rod 67 having multiple marks 672 along the rod 67, that is attached to the rail 110, for example at an area of the rail 110 that is to be positioned at a hidden side of the elevated tissue 520. When the rail 110 is transferred toward the elevated tissue 520 through the endoscope 60, or also through the multi-lumen 70, the collapsible marker rod 67 is collapsed. After the rail 110 is positioned in place around the elevated tissue 520, the collapsible marker rod 67 is erected, and its edge that is distant from the rail 110 moves along dashed line 967 in FIG. 48, from a collapsed state to an erected state, of which the erected state is shown in FIG. 48. Any mechanism for erecting the collapsible marker rod 67 is under the scope of the present subject matter. For example, the collapsible marker rod 67 is inflatable. When in the collapsed state, the collapsible marker rod 67 is deflated. In order to erect the collapsible marker rod 67, the collapsible marker rod 67 is inflated, for example with a fluid as defined above. When erected, for example in a hollow organ, like an intestine, the collapsible marker rod 67 presses an upper wall of the hollow organ, and as a result the edge of the collapsible marker rod 67 that is attached to the rail 110 fixes the rail 110 in place. An operator that observes the collapsible marker rod with the endoscope camera 602, for example along sight line 6022, can determine, according to observation and analysis of the marks 672, where the collapsible marker rod 67 is placed and whether the collapsible marker rod 67 is placed in a desired position. If not, the operator can adjust the position of the rail 110 accordingly.

Figure 49:
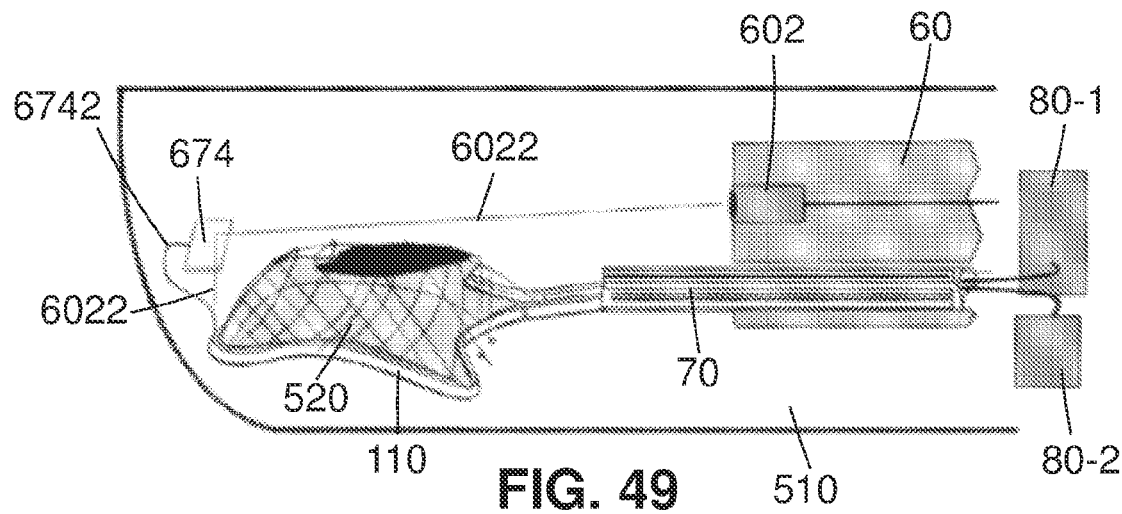
FIG. 49 schematically illustrates, according to an exemplary embodiment, a marker in a form of a collapsible mirror attached to a rail.

Referring now to FIG. 49, schematically illustrating, according to an exemplary embodiment, a marker in a form of a collapsible mirror attached to a rail. FIG. 49 shows another embodiment of the marker described in FIG. 48—a collapsible mirror 674 that is attached to the part of the rail 110 that is to be placed in a hidden area with a collapsible holder 6742. Similarly to the collapsible marker rod 67, the collapsible mirror 674 is collapsed during transfer through the endoscope 60, and occasionally through the multi-lumen 70, and when the rail 110 is deployed in place the collapsible mirror 674 is erected. The collapsible mirror 674 is positioned in an orientation that allows the operator to observe with the collapsible mirror 674, through sight line 6022 the hidden area behind the elevated tissue 520, and determine whether the rail 110 is positioned in the right place, or not.

Figure 50:
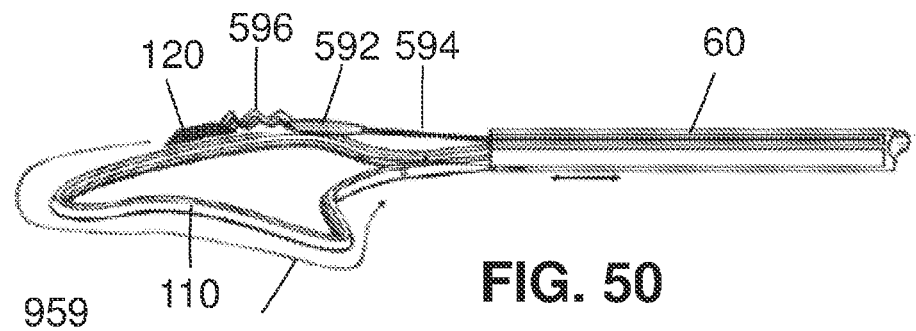
FIGS. 50-51 schematically illustrate, according to exemplary embodiments, a net for collecting a dissected elevated tissue.
Figure 51:
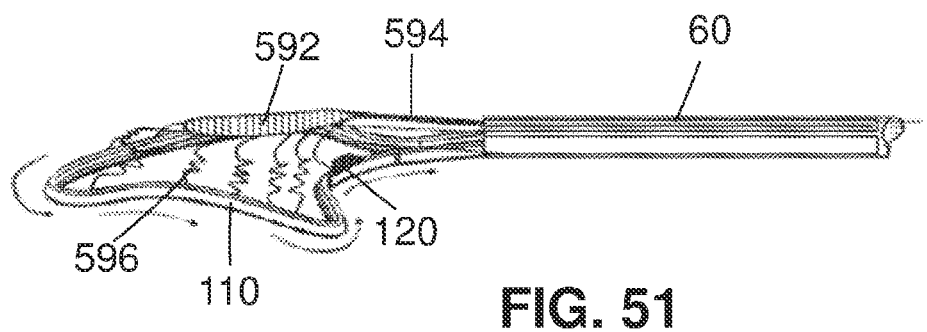

Referring now to FIGS. 50-51, schematically illustrating, according to an exemplary embodiment, a net for collecting a dissected elevated tissue. After cutting the elevated tissue 520 there is a need to remove the dissected elevated tissue 520 from the body of the patient. When the dissected elevated tissue 520 comprises malignant cells, like cancer cells, there is a need to remove the dissected elevated tissue 520 without spreading malignant cells during the removal of the dissected elevated tissue 520, in order to prevent formation of metastases. FIGS. 50-51 show a net 592 that is configured to wrap the elevated tissue 520 during the cutting of the elevated tissue 520, and during the removal of the dissected elevated tissue 520. According to one embodiment, the net 592 prevents passage of individual cells, or cell clusters, through the net 592. The net 592 is towed by the vehicle 120 during the movement of the vehicle 120 around the elevated tissue 520, in direction 959, designated with arrow 959. A net cable 594 is attached to a rear side of the net 592, relative to the direction 959 of movement of the vehicle 120. When transferred through the endoscope 60, and occasionally through the multi-lumen 70, the net is folded. When there is a need to wrap the elevated tissue 520 with the net 592, the net 592 can attach the vehicle 120 and be towed by the vehicle 120 out of the endoscope 60, or out of the multi-lumen 70. When the net 592 is in a desired place aside the elevated tissue 520, as shown in FIG. 50, the vehicle 120 continues to move along the rail 110 in direction 959, while movements of the net 592 is prevented by pulling the net cable 594 toward the endoscope 60, or multi-lumen 70. This causes deployment of the net 592 over the elevated tissue 520, as shown in FIG. 51.

According to one embodiment, strings 596 are placed between the net 592 and the vehicle 120. The strings 596 facilitate deployment of the net 592 over the elevated tissue.

After the entire dissected elevated tissue 520 is wrapped by the net 592, the rail 110 is pulled back into the endoscope 60, or into the multi-lumen 70, thereby enclosing the wrapped dissected elevated tissue 520 with the net 592. Thus, the dissected elevated tissue 520 is removed from the body without spreading cells from the elevated tissue.

Figure 52:
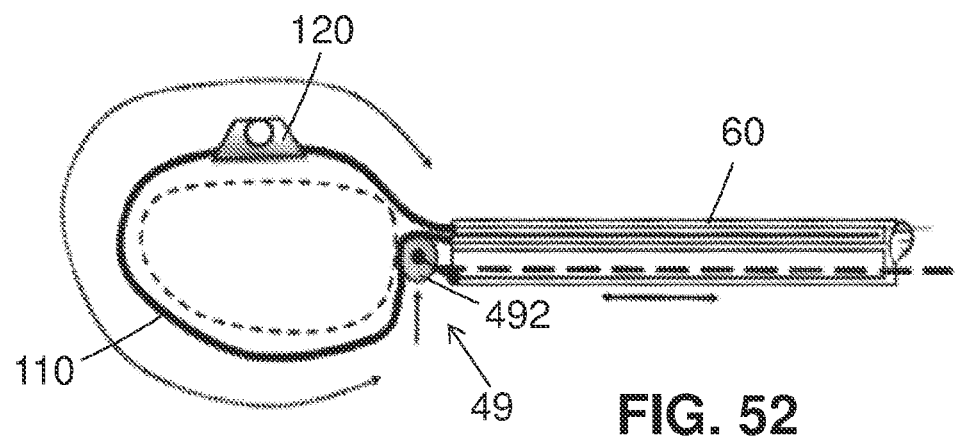
FIGS. 52-54 schematically illustrate, according to exemplary embodiments, a closing mechanism for bringing ends of a rail closer one to the other.
Figure 53:
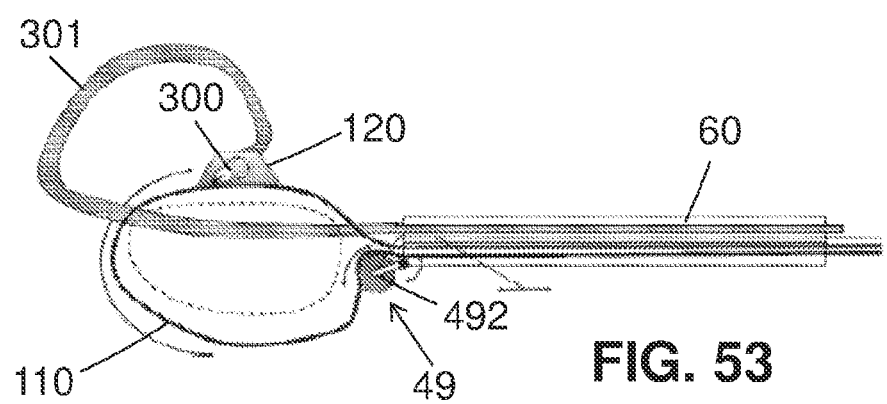
Figure 54:
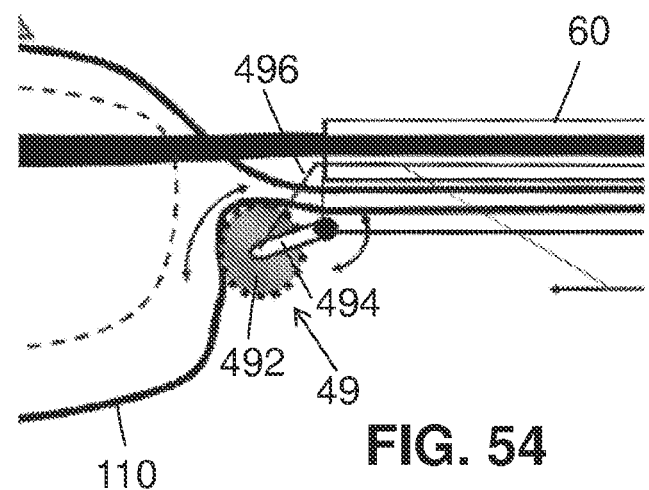

Referring now to FIGS. 52-54, schematically illustrating, according to an exemplary embodiment, a closing mechanism for bringing ends of a rail closer one to the other. When surrounding an elevated tissue 520 with the rail 110, the two ends of the rail 110 that converge to the endoscope 60, or to the multi-lumen 70, can be distant one from the other. As a result, a cutting tool 300 that is attached to the vehicle 120 cannot reach the area of the elevated tissue 520 that is aside the place of convergence of the ends of the rail 110, and the cutting of the elevated tissue 520 would not be complete.

The present subject matter provides a closing mechanism 49 for bringing the converging ends of the rail 110 closer one to the other, in order to facilitate complete cutting of the elevated tissue 520, also in the area that is aside the place of convergence of the ends of the rail 110.

FIG. 52 shows the closing mechanism 49 bringing ends of a rail 110 closer one to the other, in an area where the ends of the rail 110 converge into an endoscope 60. On the rail 110 shown in FIG. 52, there is a vehicle 120. FIG. 53 is similar to FIG. 52, and it additionally shows a cutting tool 300 connected the vehicle 120, and a cable 301 exiting the endoscope 60 and attached to the cutting tool 300. FIG. 54 shows a detailed view of the closing mechanism 49.

According to one embodiment, shown in FIG. 52, the closing mechanism 49 comprises a closing element 492 configured to push an end of the rail 110 in direction 949 towards another end of the rail 110, in a place of convergence of the two ends of the rail 110. By pushing one end of the rail 110, with the closing element 492, toward the other end of the rail 110, complete cutting of the elevated tissue 520 in this area is facilitated.

As shown in FIG. 54, the closing mechanism 49 further comprises a closing shaft 494. One end of the closing shaft 494 is pivotally connected to the closing element 492, and another end of the closing shaft 494 is pivotally connected to an edge of the endoscope 60, or multi-lumen 70, to which the two ends of the rail 110 converge. The closing element 492 can have any structure, preferably a wheel-like structure, as seen in FIGS. 52-54. In addition, a closing cable 496 is attached to the closing element 492, preferably to the point of pivotal connection of the closing element 492 with the closing shaft 494. The closing cable 496 passes from the closing element 49, through the endoscope 60, and occasionally through the multi-lumen 70, to a control panel 80. In addition, the pushing element 492 is configured to be in contact with an end of the rail 110. Pulling the closing cable 496 causes movement of the closing element 492 toward the end of the rail 110 and as a result pushing the end of the rail 110 toward the other end of the rail 110, thereby bringing both ends of the rail 110 closer one to the other.

Figure 55:
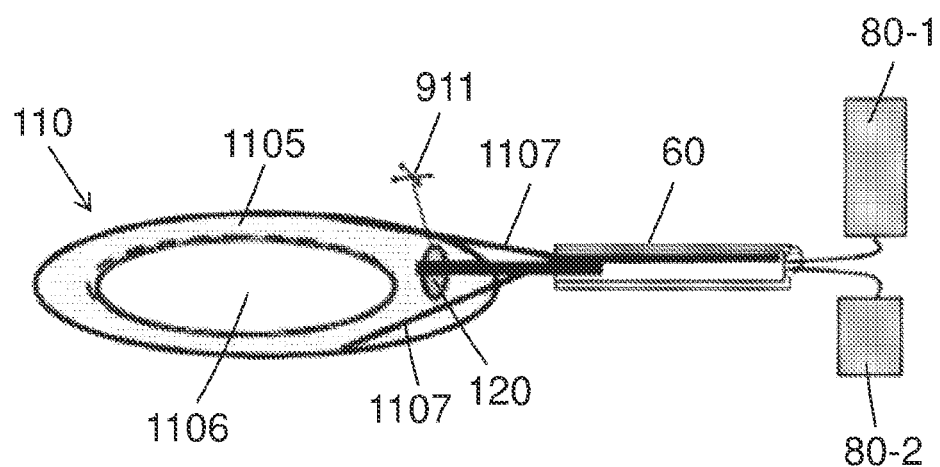
FIGS. 55-56 schematically illustrate, according to exemplary embodiments, an electromagnetic rail.
Figure 56:
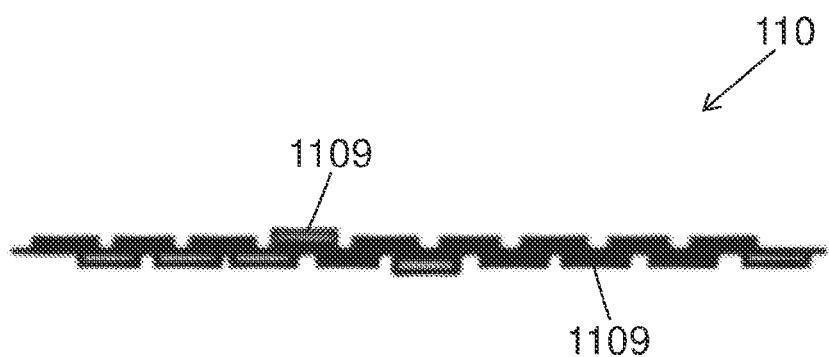

Referring now to FIGS. 55-56, schematically illustrating, according to an exemplary embodiment, an electromagnetic rail. As described above, any mechanism for moving the vehicle 120 along the rail 110 is under the scope of the present subject matter. FIGS. 55-56 show another embodiment of a rail 110 and a mechanism of moving the vehicle 120 along the rail 110. According to one embodiment, the rail 110 is an electromagnetic rail 110 in a form of an electromagnetic grid 1105 that has a ring-like structure enclosing a space 1106. The electromagnetic grid 1105 is configured to be deployed around an elevated tissue 520, when the space 1106 is configured to harbor the elevated tissue 520. Accordingly, the vehicle 120 comprises elements that are configured to be attracted to a magnetic field, for example wheels made of a metal that is magnetically attractable. When the vehicle 120 stands on the electromagnetic grid 1105, actuation of an area of the electromagnetic grid 1105 creates a magnetic field in that area that attracts the vehicle 120. Actuation of an electric field in another area of the electromagnetic grid 1105 attracts the vehicle 120 to that area and so on. This mechanism essentially allows movement of the vehicle 120 on the electromagnetic grid 1105 in ant desired direction, as indicated with arrows 911. Thus, in one hand the magnetic fields generated in the electromagnetic grid 1105 drive movement of the vehicle 120, and on the other hand, the magnetic fields facilitate attachment of the vehicle 120 to the electromagnetic rail 110.

Any mechanism for deploying the electromagnetic grid 1105 from the endoscope 60, or the multi-lumen 70, is under the scope of the present subject matter, for example a couple of deployment arms 1107 that are attached to the electromagnetic grid 1105 and are configured to exit the endoscope 60, or the multi-lumen 70, and deploy the electromagnetic grid 1105 in a desired place.

FIG. 56 shows a side view of an exemplary design of the electromagnetic grid 1105. According to one embodiment, the electromagnetic grid comprises multiple electromagnetic elements 1109, arranged in two layers and having gaps in between them, while an electromagnetic element 1109 of one layer overlaps with a gap in the other layer.

The present subject matter further provides a method for cutting an elevated tissue in a body of a patient, the method comprising:
  inserting a rail to a vicinity of the elevated tissue;
  surrounding the elevated tissue with the rail;
  placing a vehicle on the rail;
  connecting a cutting device to the vehicle;
  moving the vehicle along the rail while cutting the elevated tissue with the cutting device.

According to one embodiment, the inserting of the rail into the body of the patient is with an endoscope.

According to one embodiment, the cutting of the elevated tissue is controlled with a control panel operable through the endoscope.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A system for allowing controlled access of a tool to all sides of an elevated tissue in a body of a patient, the system comprising:
  a rail configured to surround the elevated tissue and to be inserted into the body of the patient through an endoscope;
  at least one vehicle configured to move along the rail and carry at least one tool that is configured to manipulate the elevated tissue; and
  a manifold head configured to store the vehicle during transfer through the endoscope.

2. The system of claim 1, wherein at least one connector is attached to the vehicle, and configured to connect the at least one tool to the vehicle.

3. The system of claim 1, wherein the at least one vehicle is configured to be inserted into the body of the patient through an endoscope.

4. The system of claim 1, wherein the tool is a cutting tool comprising a blade configured to cut the elevated tissue.

5. The system of claim 1, wherein the vehicle further comprises an imaging device.

6. The system of claim 5, wherein the vehicle further comprises at least one light source.

7. The system of claim 1, wherein a vehicle cable is attached to the vehicle, and wherein movement of the vehicle along the rail is driven by pushing and pulling the vehicle cable.

8. The system of claim 7, wherein the vehicle cable resides inside the rail.

9. The system of claim 8, wherein the rail further comprises balls that are configured to be in contact with the vehicle cable and rotate when the vehicle cable is pushed or pulled, for facilitating smooth movement of the vehicle cable inside the rail.

10. The system of claim 1, wherein movement of the vehicle along the rail is driven manually.

11. The system of claim 1, wherein the vehicle further comprises at least one bearing configured to roll over the rail and reduce friction forces exerted on the vehicle during the movement of the vehicle along the rail.

12. The system of claim 1, wherein the vehicle further comprises a drive wheel configured to roll over the rail and drive the movement of the vehicle, and a motor configured to provide kinetic energy to the drive wheel.

13. The system of claim 1, wherein the rail is configured to assume any structure in any dimension, and adapt the structure of the rail to a contour and surface features of the elevated tissue that the rail surrounds, and a surface tissue on which the rail resides.

14. The system of claim 1, wherein a vehicle surface of the rail is toothed.

15. The system of claim 14, wherein the vehicle comprise at least one toothed wheel configured to be in contact with and roll along the toothed vehicle surface.

16. A method for cutting an elevated tissue in a body of a patient, the method comprising:
  inserting a rail to a vicinity of the elevated tissue by using an endoscope, while a vehicle is stored in a manifold head during transfer through the endoscope;
  surrounding the elevated tissue with the rail;
  placing the vehicle on the rail;
  connecting a cutting device to the vehicle; and
  moving the vehicle along the rail while cutting the elevated tissue with the cutting device.

17. The method of claim 16, wherein the cutting of the elevated tissue is controlled with a control panel operable through the endoscope.

18. A system for allowing controlled access of a tool to all sides of an elevated tissue in a body of a patient, the system comprising:
  a rail configured to surround the elevated tissue;
  at least one vehicle comprising an imaging device and configured to move along the rail and carry at least one tool that is configured to manipulate the elevated tissue.

19. The system of claim 18, wherein the rail is configured to be inserted into the body of the patient through an endoscope.

20. The system of claim 19, wherein the system further comprises a manifold head configured to store the vehicle during transfer through the endoscope.

21. The system of claim 18, wherein the at least one vehicle is configured to be inserted into the body of the patient through an endoscope.

22. The system of claim 18, wherein the vehicle further comprises at least one light source.

23. A method for cutting an elevated tissue in a body of a patient, the method comprising:
   inserting a rail to a vicinity of the elevated tissue;
   surrounding the elevated tissue with the rail;
   placing a vehicle comprising an imaging device on the rail;
   connecting a cutting device to the vehicle; and
   moving the vehicle along the rail while cutting the elevated tissue with the cutting device.

24. The method of claim 23, wherein the inserting of the rail into the body of the patient is performed using an endoscope.

25. The method of claim 24, wherein the cutting of the elevated tissue is controlled with a control panel operable through the endoscope.

\* \* \* \* \*